United States Patent [19]

Heckendorn et al.

[11] 4,209,516
[45] Jun. 24, 1980

[54] TRIAZOLE DERIVATIVES

[75] Inventors: Roland Heckendorn, Arlesheim; René Meier, Buus, both of Switzerland

[73] Assignee: Ciba-Geigy Corporation, Ardsley, N.Y.

[21] Appl. No.: 938,623

[22] Filed: Aug. 31, 1978

Related U.S. Application Data

[63] Continuation of Ser. No. 746,654, Dec. 2, 1976, abandoned, which is a continuation-in-part of Ser. No. 584,801, Jun. 9, 1975, abandoned.

[30] Foreign Application Priority Data

Jun. 14, 1974 [CH] Switzerland .................. 8175/74

[51] Int. Cl.² .................. A61K 31/41; C07D 249/10; C07D 401/06; C07D 413/06
[52] U.S. Cl. .................. 424/248.54; 260/193; 260/243.3; 260/245.5; 260/244.4; 260/308 R; 544/58.5; 544/82; 544/130; 544/132; 544/364; 544/366; 546/190; 546/194; 546/210; 424/232; 424/267; 424/269; 548/269
[58] Field of Search .......... 260/308 R, 293.63, 293.69; 544/130, 132, 82; 424/269, 248.53, 248.54, 248.55, 267; 546/190, 194, 210

[56] References Cited

U.S. PATENT DOCUMENTS

| | | | |
|---|---|---|---|
| 3,784,556 | 1/1974 | Gagneux et al. | 260/308 R |
| 3,856,792 | 12/1974 | Hester | 260/308 R |
| 3,862,171 | 1/1975 | Gagneux et al. | 260/308 R |
| 3,870,714 | 3/1975 | Gagneux et al. | 260/308 R |
| 3,878,205 | 4/1975 | Gagneux et al. | 260/308 R |
| 3,907,821 | 9/1975 | Gall | 260/308 R |

Primary Examiner—Alton D. Rollins
Attorney, Agent, or Firm—John J. Maitner

[57] ABSTRACT

The present invention relates to new triazole derivatives of the formula

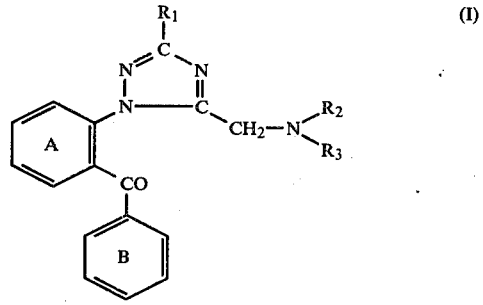

wherein
$R_1$ represents hydrogen, lower alkyl, optionally esterified or etherified hydroxymethyl, formyl, optionally functionally modified carboxy, or optionally mono- or disubstituted aminomethyl,
$R_2$ represents lower alkyl, and $R_3$ represents hydrogen or lower alkyl, whereby $R_2$ and $R_3$ as lower alkyl can be bound directly, or in β- or γ-position also by way of oxygen, sulphur or the imino radical or a lower alkylimino radical, and the rings A and B independently of each other can be unsubstituted or substituted, and to their addition salts with inorganic and organic acids, in particular the pharmaceutically acceptable acid addition salts. These new compounds possess valuable pharmacological properties. In particular they have an anti-convulsive activity and are useful for the treatment of epilepsy and of conditions of tension and of agitation. Specific embodiments are 1-[2-(o-chlorobenzoyl)-4-chlorophenyl]-5-(morpholinomethyl)-1H-1,2,4-triazole-3-carboxamide, 1-[2-(o-chlorobenzoyl)-4-chlorophenyl]-5-[(dimethylamino)-methyl]-1H-1,2,4-tariazole-3-carboxamide, N-methyl-1-[2-(o-chlorobenzoyl)-4-chlorophenyl]-5-(morpholinomethyl)-1H-1,2,4-triazole-3-carboxamide, N-ethyl-1-[2-(o-chlorobenzoyl)-4-chlorophenyl]-5-(morpholinomethyl)-1H-1,2,4-triazole-3-carboxamide, N-ethyl-1-[2-(o-chlorobenzoyl)-4-chlorophenyl]-5-[(dimethylamino)-methyl]-1H-1,2,4-triazole-3-carboxamide, N-propyl-1-[2-(o-chlorobenzoyl)-4-chlorophenyl]-5-[(dimethylamino)-methyl]-1H-1,2,4-triazole-3-carboxamide, N,N-dimethyl-1-[2-(o-chlorobenzoyl)-4-chlorophenyl]-5-[(dimethylamino)-methyl]-1H-1,2,4-triazole-3-carboxamide, and N,N-dimethyl-1-[2-(o-fluorobenzoyl)-4-chlorophenyl]-5-[(dimethylamino)-methyl]-1H-1,2,4-triazole-3-carboxamide.

20 Claims, No Drawings

TRIAZOLE DERIVATIVES

This is a continuation of application Ser. No. 746,654 filed on Dec. 2, 1976, now abandoned, which in turn is a continuation-in-part of application Ser. No. 584,801 filed June 9, 1975, now abandoned.

The present invention relates to processes for the production of new triazole derivatives and their acid addition salts, to these new substances themselves and to pharmaceutical compositions containing them, as well as to the therapeutic application of the new substances.

The new triazole derivatives according to the invention correspond to the general formula I

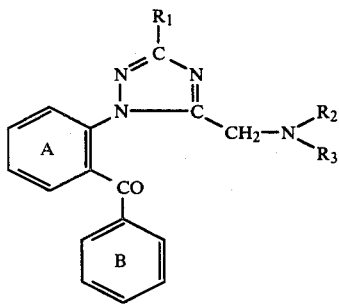

in which
R₁ represents hydrogen, lower alkyl, optionally esterified or etherified hydroxymethyl, formyl, optionally functionally modified carboxy, or optionally mono- or disubstituted aminomethyl,
R₂ represents lower alkyl, and
R₃ represents hydrogen or lower alkyl, whereby R₂ and R₃ as lower alkyl can be bound directly, or in β- or γ-position also by way of oxygen, sulphur or the imino radical or a lower alkylimino radical, and the rings A and B independently of each other can be unsubstituted or substituted.

The invention relates also to the addition salts of the triazole derivatives of the general formula I with inorganic and organic acids.

In the triazole derivatives of the general formula I, $R_1$ as lower alkyl is, e.g., ethyl, propyl, butyl, isobutyl, pentyl, isopentyl, neopentyl (2,2-dimethylpropyl), hexyl or isohexyl and, in particular, methyl; as esterified hydroxymethyl it is, e.g., lower alkanoyloxymethyl such as formyloxymethyl, propionyloxymethyl, butyryloxymethyl, pivaloyloxymethyl and, in particular, acetoxymethyl; and as etherified hydroxymethyl it is, e.g., loweralkoxymethyl such as methoxy-, ethoxy-, propoxy-, isopropoxy-, butoxy-, isobutoxy-, sec.butoxy-, pentyloxy-, isopentyloxy-, neopentyloxy-, hexyloxy- or isohexyloxymethyl. As functionally modified carboxy, $R_1$ is, e.g., esterified carboxy, especially lower alkoxycarbonyl such as propoxycarbonyl, butoxycarbonyl, isobutyloxycarbonyl, pentyloxycarbonyl, isopentyloxycarbonyl, hexyloxycarbonyl and, in particular, methoxycarbonyl or ethoxycarbonyl; also cyano and, optionally, mono- or di-substituted carbamoyl. Substituents of carbamoyl groups $R_1$ as well as of aminomethyl groups $R_1$ are on the one hand, in particular, monovalent hydrocarbon radicals having at most 10 carbon atoms, such as lower alkyl, e.g. propyl, isopropyl, butyl, isobutyl, sec.butyl, pentyl, isopentyl, neopentyl, hexyl or heptyl, and especially methyl or ethyl, or araliphatic hydrocarbon radicals having 7 to 10 carbon atoms, e.g. benzyl, phenethyl, α-, o-, m- or p-methylbenzyl, 3-phenylpropyl, 2-phenylpropyl, α-methylphenethyl, 4-phenylbutyl or p-isopropylbenzyl; and on the other hand two lower alkyl radicals bound analogously to the definition for $R_2$ and $R_3$ either directly or in the β- or γ-position also by way of oxygen, sulphur, the imino radical or a lower alkylimino radical, which lower alkyl radicals form together with the adjacent nitrogen atoms, e.g., the 1-aziridinyl, 1-azetidinyl, 1-pyrrolidinyl, piperidino, hexahydro-1H-azepin-1-yl, morpholino, thiomorpholino, 1-piperazinyl or hexahydro-1H-1,4-diazepin-1-yl group, whereby the two last-mentioned groups may be substituted in the 4-position, i.e. in the imino group, e.g., by methyl, ethyl, propyl, isopropyl, butyl or isobutyl, and all aforementioned cyclic groups on carbon atoms also by ethyl, propyl or, in particular, methyl.

The lower alkyl $R_2$ and the radical $R_3$ as lower alkyl are, for example, propyl, isopropyl, butyl, isobutyl, sec.butyl, pentyl, isopentyl, neopentyl, hexyl or heptyl, and particularly methyl or ethyl. Bound together in the above-defined manner, $R_2$ and $R_3$ together with the adjacent nitrogen atom form, for example, the cyclic groups mentioned above in connection with the meaning of $R_1$, especially 1-pyrrolidinyl, piperidino or morpholino.

Where reference is made in the foregoing and in the following to lower groups, then those meant are groups having at most 7 carbon atoms and preferably at most 4 carbon atoms.

The rings A and B can each on its own be repeatedly substituted: but ring A is preferably monosubstituted and ring B preferably unsubstituted or disubstituted and, in particular, monosubstituted. The substituents are, for example, halogen up to atomic number 35, trifluoromethyl, nitro, lower alkyl or lower alkoxy. A substituent of the ring A is preferably in the 4-position with respect to the triazole ring, and the substituent(s) of the ring B in the one (or in both) ortho-position(s) with respect to the carbonyl group. Halogen atoms as substituents of the rings A and B are fluorine, chlorine or bromine atoms; lower alkyl is, for example, methyl, ethyl, propyl, isopropyl, butyl, isobutyl, tert.butyl, pentyl, isopentyl, neopentyl, tert.pentyl, hexyl or heptyl; and lower alkoxy is, for example, methoxy, ethoxy, propoxy, isopropoxy, butoxy, isobutoxy, pentyloxy, isopentyloxy, hexyloxy or heptyloxy. A substituent of the ring A, preferably in the 4-position to the triazole ring, is, in particular, one of the mentioned halogen atoms, especially chlorine, also nitro or trifluoromethyl. The ring B is preferably unsubstituted, or substituted by fluorine, chlorine, bromine or trifluoromethyl in any position, particularly, however, by fluorine or chlorine in the o-position.

The triazole derivatives of the general formula I and their addition salts with inorganic and organic acids possess valuable pharmacological properties. They have, in particular, an anticonvulsive action, as can be verified, for example, on the mouse in the pentetrazole convulsion test after administration of oral doses of from about 0.3 mg/kg, as well as in the strychnine convulsion test and in the electroshock test after administration in each case of oral doses of from about 1 mg/kg, for example of 1-[2-(o-chlorobenzoyl)-4-chlorophenyl]-5-(morpholinomethyl)-1H-1,2,4-triazole-3-carboxamide, 1-[2-(o-chlorobenzoyl)-4-chlorophenyl]-5-[(dimethylamino)-methyl]-1H-1,2,4-triazole-3-carboxamide, N-methyl-1-[2-(o-chlorobenzoyl)-4-chlorophenyl]-5-(morpholinomethyl)-1H-1,2,4-triazole-3-carboxamide, N-ethyl-1-[2-(o-chlorobenzoyl)-4-chlorophenyl]-5-(morpholinomethyl)-1H-1,2,4-triazole-3-carboxamide, N-ethyl-1-[2-(o-chlorobenzoyl)-4-chlorophenyl]-5-[(dimethylamino)-methyl]-1H-1,2,4-triazole-3-carboxamide, N-propyl-1-[2-(o-chlorobenzoyl)-4-chlorophenyl]-5-[(dimethylamino)-methyl]-1H-1,2,4-triazole-3-carboxamide, N,N-dimethyl-1-[2-(o-chlorobenzoyl)-4-chlorophenyl]-5-[(dimethylamino)-methyl]-1H-1,2,4-triazole-3-carboxamide, and N,N-dimethyl-1-[2-(o-fluorobenzoyl)-4-chlorophenyl]-5-[(dimethylamino)-methyl]-1H-1,2,4-triazole-3-carboxamide.

Furthermore, the triazole derivatives of the general formula I and their acid addition salts also have a moderate central depressant action. The mentioned properties, together with others that can be demonstrated by selected standard tests [see W. Theobald and H. A. Kunz, Arzneimittelforsch. 13, 122 (1963) as well as W. Theobald et al., Arzneimittel-forsch. 17, 561 (1967)], characterise the triazole derivatives of the general formula I and their pharmaceutically acceptable addition salts with inorganic and organic acids as being active substances for anticonvulsants and tranquillisers which are usable for the treatment of epilepsy and of conditions of tension and agitation. Various triazole derivatives of the general formula I are moreover suitable as intermediates for the production of further compounds embraced by this general formula.

The invention relates, in particular, to triazole derivatives of the general formula I in which $R_1$, $R_2$ and $R_3$ have the meanings given under this formula, ring A is substituted in the 4-position with respect to the triazole ring by halogen up to atomic number 35, especially by chlorine, or by nitro or trifluoromethyl, and ring B is unsubstituted, or substituted in any position by halogen up to atomic number 35 or by trifluoromethyl, preferably however by fluorine or chlorine in the ortho-position. Particularly important triazole derivatives within the scope of the general formula I—as triazole derivatives of the general formula I a—as well as within the more restricted compound group defined in the foregoing, are, with regard to their pharmacological properties, those wherein $R_1$ is a group of the partial formula I aa

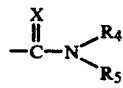
(I aa)

in which

X represents oxygen or two hydrogen atoms, and $R_4$ and $R_5$, as described previously with respect to the substitution of aminomethyl groups and carbamoyl groups $R_1$, each independently represent hydrogen or hydrocarbon radicals each having at most 10 carbon atoms, which radicals, provided that they are lower alkyl, can also be bound directly together or in the β- or γ-position by way of oxygen, sulphur, the imino radical or a lower alkylimino radical. Where $R_4$ and $R_5$ do not represent hydrogen, they correspond in particular to the definition for $R_2$ and $R_3$ given under formula I: preferably, however, they each independently represent hydrogen or lower alkyl having at most 3 carbon atoms, namely methyl, ethy, propyl or isopropyl, or together with the adjacent nitrogen atom they represent morpholino, or alkyleneimino having 5 to 6 ring members, such as 1-pyrrolidinyl or piperidino. In this group of compounds, $R_2$ and $R_3$ have the meanings given under formula I; they represent however preferably methyl or ethyl, or together with the adjacent nitrogen atom they represent morpholino or alkyleneimino having 5 to 6 ring members, such as 1-pyrrolidinyl or piperidino, while the rings A and B are independently of each other unsubstituted or substituted, and in the latter case they preferably carry the above-mentioned groups of substituents and, in particular, the specifically mentioned substituents.

Triazole derivatives of the general formula I wherein $R_1$ represents hydroxymethyl, formyl, carboxyl or lower alkoxycarbonyl, while $R_2$ and $R_3$ have the meanings given under formula I or preferably the more restricted meanings given in the foregoing, and the rings A and B can be substituted as given under formula I, preferably however in the manner previously specified, are especially important as intermediates for the production of other pharmacologically valuable compounds embraced by the general formula I, as well as of other such compounds. Compounds of the general formula I having a carboxy group or lower alkoxy carbonyl group as $R_1$ are of particular importance as intermediates on account of the case with which they can be produced.

The data given in the foregoing relate likewise to the addition salts of the stated triazole derivatives embraced by the general formula I with inorganic and organic acids, especially to the pharmaceutically acceptable acid addition salts.

The new triazole derivatives of the general formula I and their acid addition salts are produced according to the invention by a process wherein (a) a reactive ester of a compound of the general formula II

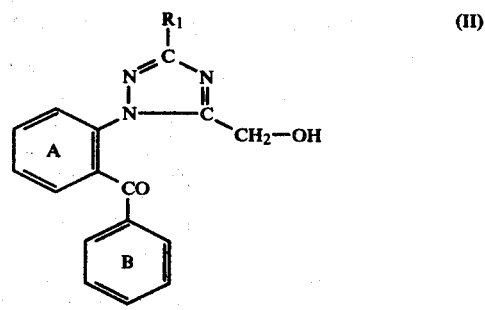
(II)

in which $R_1$ has the meaning given under formula I, and the rings A and B can be substituted as given there, is reacted with a compound of the general formula III

(III)

wherein $R_2$ and $R_3$ have the meanings given under formula I, or with an alkali metal derivative of such a compound in which $R_3$ has a meaning other than hydrogen; or (b), for the production of compounds of the general formula I wherein $R_2$ and $R_3$ represent methyl, while $R_1$ has the meaning given under formula I, a compound of the general formula IV

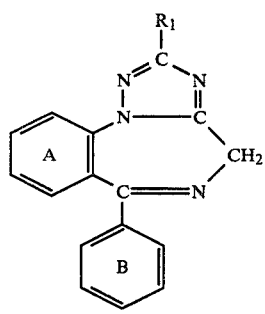 (IV)

in which $R_1$ has the meaning given under formula I, and the rings A and B can be substituted as given there, is reacted with formaldehyde and formic acid; or (c), for the production of compounds of the general formula I wherein $R_1$ has the meaning given under formula I with the exception of hydroxymethyl, while $R_2$ and $R_3$ have the meanings given under formula I, a compound of the general formula V

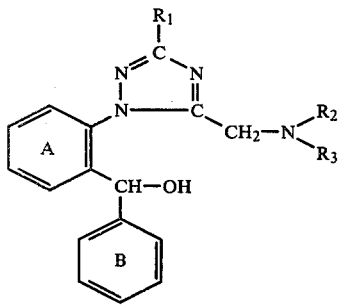 (V)

in which
$R_1$, $R_2$ and $R_3$ have the meanings given under formula I, and the rings A and B can be substituted as given there, is oxidised; or (d), for the production of compounds of the general formula I wherein $R_1$ represents carboxy or lower alkoxy-carbonyl, while $R_2$ and $R_3$ have the meanings given under formula I, a basic medium is allowed to react with a compound of the general formula VI

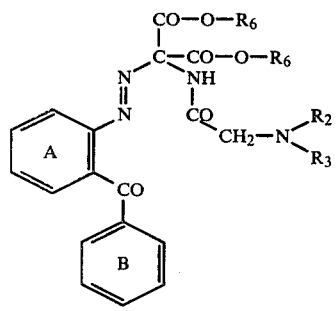 (VI)

in which
$R_6$ represents lower alkyl,
$R_2$ and $R_3$ have the meanings given under formula I, and the rings A and B can be substituted as defined there;

and, optionally, a compound I obtained by any one of the processes given under (a) to (d) is converted into an addition salt with an inorganic or organic acid.

In triazole derivatives embraced by the general formula I, it is possible, within the limits of the definition for these compounds, to introduce, split off or modify substituents in the usual manner, i.e. to convert triazole derivatives of the general formula I in the usual manner into other final materials of the general formula I as defined. Thus, compounds of the general formula I are obtained by a process wherein (e), for the production of compounds of the general formula I wherein $R_1$ represents optionally mono- or disubstituted carbamoyl, while $R_2$ and $R_3$ have the meanings given under formula I, a carboxylic acid of the general formula I e embraced by the general formula I

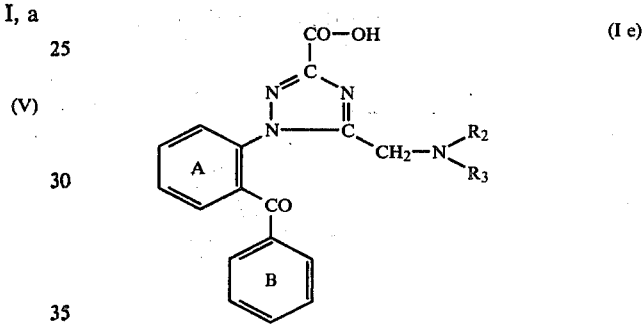 (I e)

in which $R_2$ and $R_3$ have the meanings given under formula I, and the rings A and B can be substituted as given there, or a reactive functional derivative of such a carboxylic acid, is reacted with a compound of the general formula VII

 (VII)

in which
$R_4$ and $R_5$ each independently represent hydrogen or hydrocarbon radicals each having at most 10 carbon atoms, which, provided that they represent lower alkyl, can also be bound directly together, or they can be bound in the β- or γ-position by way of oxygen, sulphur, the imino radical or a lower alkylimino radical,
or with a reactive functional derivative of such a compound; or (f), for the production of compounds of the general formula I wherein $R_1$ is aminomethyl or mono- or disubstituted aminomethyl, while $R_2$ and $R_3$ have the meanings given under the general formula I, a reactive ester of a compound of the general formula I f embraced by the general formula I

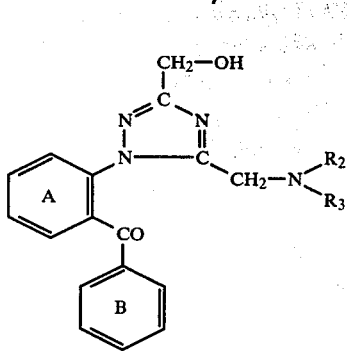

(I f)

in which $R_2$ and $R_3$ have the meanings given under formula I, and the rings A and B can be substituted as given there, is reacted with a compound of the general formula VII given above, wherein $R_4$ and $R_5$ have the meanings given under this formula, or with an alkali metal derivative of such a compound; or (g), for the production of a triazole derivative of the general formula I wherein $R_1$ represents hydroxymethyl, while $R_2$ and $R_3$ have the meanings given under formula I, a compound of the general formula VIII

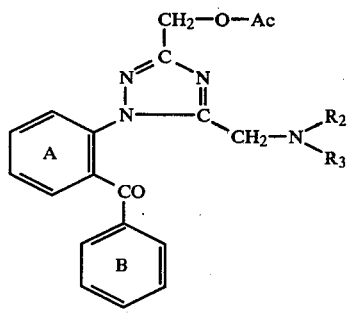

(VIII)

in which
Ac represents the acyl radical of an organic acid, $R_2$ and $R_3$ have the meanings given under formula I, and the rings A and B can be substituted as defined there, is solvolysed; or (h), for the production of a triazole derivative of the general formula I wherein $R_1$ represents formyl, while $R_2$ and $R_3$ have the meanings given under formula I, a compound of the general formula I h

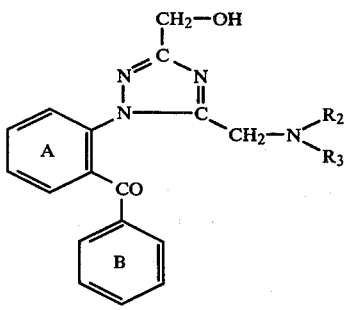

(I h)

in which $R_2$ and $R_3$ have the meanings given under formula I, and the rings A and B can be substituted as given there, is oxidised; or (i), for the production of a triazole derivative of the general formula I wherein $R_1$ represents cyano, while $R_2$ and $R_3$ have the meanings given under formula I, a compound of the general formula I i

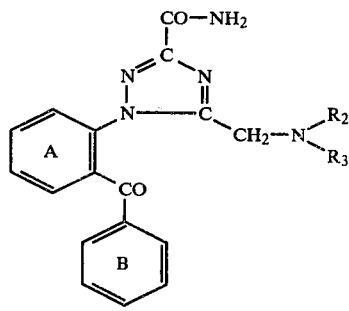

(I i)

in which $R_2$ and $R_3$ have the meanings given under formula I, and the rings A and B can be substituted as given there, is dehydrated; or (j), for the production of triazole derivatives of the general formula I wherein $R_1$ represents optionally mono- or disubstituted carbamoyl, while $R_2$ and $R_3$ have the meanings given under formula I, a compound of the general formula I j embraced by the general formula I

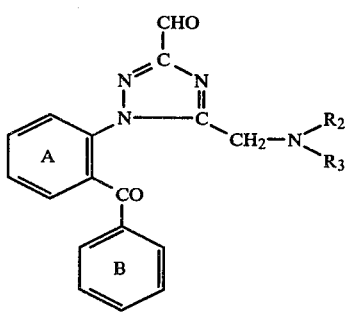

(I j)

in which $R_2$ and $R_3$ have the meanings given under formula I, and the rings A and B can be substituted as given there, is represented with a compound of the general formula VII previously given, wherein $R_4$ and $R_5$ have the meanings given under formula VII, in the presence of an alkali metal cyanide and of a selective oxidising agent; and, optionally, a triazole derivative of the general formula I obtained by any one process or by several successive processes according to (e) to (j) is converted into an addition salt with an inorganic or organic acid.

For process (a), suitable reactive esters of hydroxy compounds of the general formula II are, for example, hydrohalic acid esters such as chlorides and bromides, as well as the iodides produced from these, optionally in situ not until immediately before the subsequent reaction. Further suitable reactive esters of compounds of the general formula II are sulphonic acid esters thereof, particularly lower alkanesulphonic acid esters such as the methanesulphonic acid esters, and arenesulphonic acid esters, such as the o- and p-toluenesulphonic acid esters, the o- or p-nitrobenzenesulphonic acid esters or the o- or p-chlorobenzenesulphonic acid esters. The reactions with compounds of the general formula III are preferably preformed in the presence of an acid-binding agent. As the acid-binding agent, it is possible to use an excess of the compound of the general formula III, or, e.g., also a tertiary organic base such as ethyl-diisopropylamine or collidine, or an inorganic basic substance such as potassium carbonate. The reaction medium employed can be, e.g., an inert, optionally hydrous, solvent, e.g. a lower alkanol such as methanol, ethanol, propanol, isopropanol or butanol, a ketone such as acetone or methyl ethyl ketone, also, e.g., dioxane, tetrahydrofuran, dimethylformamide or dimethylsulphoxide, or an excess of the compound of the general formula III, as such or as an aqueous or organic solution.

If there is used as reactant, instead of the compound of the general formula III, an alkali metal derivative of such a compound, e.g. a sodium, lithium or potassium derivative, then as solvent there are preferably used hydrocarbons such as benzene, toluene or xylene, ethereal liquids such as 1,2-dimethoxyethane, tetrahydrofuran or dioxane, acid amides such as dimethylformamide or N,N,N',N',N'',N''-hexamethyl-phosphoric acid triamide, or sulphoxides such as dimethylsulphoxide. The alkali metal derivatives of such compounds of the general formula III in which $R_3$ has a meaning other than hydrogen are formed preferably in situ, e.g. by the addition of an at least equimolar amount of alkali metal hydride such as sodium hydride, alkali metal amide such as sodium amide or lithium amide, or of an alkali-metal-loorganic compound such as phenyl- or butyllithium. The reaction temperature is preferably between 0° and 120° C., or it is the boiling temperature of the reaction medium employed.

Some chlorides of compounds of the general formula II are described, as intermediates, in the German 'Offenlegungsschriften' Nos. 2,159,527, 2,215,943 and 2,304,307. Other reactive esters of compounds of the general formula II can be produced analogously.

In the splitting of the diazepine ring according to Process (b) by means of formaldehyde and formic acid, the result is not only that the amino group previously belonging to the diazepine ring is dimethylated, but also that an optionally present aminomethyl and monosubstituted aminomethyl $R_1$ is di- and monomethylated, respectively. The splitting according to the process is performed at elevated temperature, preferably at about 80° C. up to the boiling temperature of the reaction mixture. Although not absolutely necessary with respect to the overall balanced of the reaction, an appreciable content of water in the reaction mixture is advantageous; it is therefore possible to use either aqueous, e.g., 30 to 36% formaldehyde solution or aqueous, e.g., 85 to 95% formic acid. The formaldehyde is preferably used in a considerable excess, e.g. two to five times the theoretical amount of 2 to 4 moles per mole of starting material of the general formula IV, and the formic acid in an even greater excess, e.g., two to five times the molar amount relative to the formaldehyde. Of the starting materials of the general formula IV, those with hydrogen, carboxy or lower alkoxycarbonyl as $R_1$ are described in the German 'Offenlegungsschriften' Nos. 2,159,527 and 2,215,943, those with lower alkyl or hydrogen as $R_1$ in the German 'Offenlegungsschriften' Nos. 2,055,889 and 2,159,527, those with optionally mono- or disubstituted aminomethyl or with hydroxymethyl as $R_1$ in the German 'Offenlegungsschrift' No. 2,234,652, and those with optionally mono- or disubstituted carbamoyl or with formyl as $R_1$ in the German 'Offenlegungsschrift' No. 2,304,307. Further compounds of the general formula IV can be produced by methods analogous to those described in the aforementioned 'Offenlegungsschriften'.

The oxidation according to Process (c) is performed, for example, by means of a higher metal oxide such as chromium trioxide, e.g. dissolved in acetic acid, or dissolved in dilute sulphuric acid as oxidation solution according to Jones and gradually added to the solution of the starting material in acetone, at a temperature of between about 0° and 60° C., preferably at 20°–30° C.; or with manganese dioxide, particularly in the activated form described by J. Attenburrow et al., *J. Chem. Soc.* 1952, 1104, in an inert organic solvent, such as benzene or dioxane, at temperatures of between room temperature and the boiling temperature of the reaction medium.

Starting materials of the general formula V are obtained, for example, by reduction of reactive esters of compounds of the general formula II, especially chlorides, with an alkali metal borohydride, such as sodium borohydride, in a lower alkanol such as methanol, or in some other suitable organic solvent such as tetrahydrofuran, at low temperatures, preferably between about −20° C. and 0° C., and reaction of the resulting reduction products with compounds of the general formula III in a manner analogous to that in Process (a).

Furthermore, starting materials of the general formula V can be obtained, e.g., also by reduction of compounds of the general formula I, whereby a suitable reduction process or catalytic hydrogenation, e.g. in the presence of Raney nickel or of a noble metal catalyst, such as palladium on charcoal or on an alkaline-earth metal carbonate, can be selected in the case where groups $R_1$ that are in themselves reducible are to be retained intact. The oxidation according to (c), together with the preceding reduction, is however more advantageously applied to such compounds of the general formula I which contain a group $R_1$ the reduction of which is desired but not possible, or only possible with difficulty, without the simultaneous reduction of the carbonyl group situated between the rings A and B. For example, a compound of the general formula I in which $R_1$ is disubstituted carbamoyl can be reduced by means of a complex hydride, such as lithium aluminium hydride, in an ethereal solvent, such as tetrahydrofuran, to a compound of the general formula V in which $R_1$ is the corresponding disubstituted aminomethyl. In addition, it is possible in an analogous manner to reduce a compound of the general formula I wherein $R_1$ is lower alkoxycarbonyl to a compound of the general formula V wherein $R_1$ is hydroxymethyl. If the reduction product is thereupon directly oxidised, then the hydroxymethyl group $R_1$ is attacked before the hydroxymethylene group, and there is firstly formed, depending on the oxidising agent used, a formyl group or carboxyl group $R_1$, and immediately afterwards there occurs in the same operation the oxidation of the hydroxymethylene group to the carbonyl group. Since compounds of the general formula I having a carboxy group $R_1$ are more easily obtainable in another manner, particularly the oxidation of a hydroxymethyl group $R_1$ to a formyl group $R_1$ in an analogous manner to that of Process (h), e.g. by means of the above-mentioned oxidation solution according to Jones, in the same operation as the oxidation of the hydroxymethylene group according to Process (c) is of practical importance. Alternatively, it is possible in an above-mentioned reduction product to also firstly selectively acylate, e.g. acetylate, the hydroxymethyl group $R_1$, to then carry out oxidation according to (c) and, optionally, to subsequently again liberate the hydroxymethyl group according to Process (g).

Cyclisation of compounds of the general formula VI according to (d) is performed, e.g., in a diluted aqueous or aqueous-organic alkali hydroxide solution, especially sodium hydroxide or potassium hydroxide solution, as a basic medium, at room temperature or at moderately elevated temperatures up to the boiling temperature of the reaction medium. The organic solvent used is, e.g., dioxane or a lower alkanol such as ethanol. If mild reaction conditions are chosen, e.g. if the at most double-molar amount, relative to the compound of the general formula VI, of alkali hydroxide is allowed to react at room temperature, and the reaction mixture is neutralised before processing, then as the main product there is obtained a triazole derivative of the general formula I in which $R_1$ is the lower alkoxy carbonyl corresponding to the group $R_6$; whilst under less mild conditions the corresponding carboxylic acid, i.e. the compound of the general formula I having carboxy as $R_1$, is obtained. Cyclisation can also be performed by means of an aqueous-organic ammonia solution as basic medium, e.g. in a mixture of concentrated aqueous ammonia and dimethylformamide.

Starting materials of the general formula VI are obtained, for example, by reaction of the analogous compounds described, as intermediates, e.g., in the German 'Offenlegungsschriften' Nos. 2,159,527, 2,215,943 and 2,304,307, which compounds contain a halogen atom, especially a chlorine atom, instead of the disubstituted amino group, with a compound of the previously given general formula III in which $R_2$ and $R_3$ have the meanings defined there, or with an alkali metal derivative thereof, analogously to Process (a) for the production of the triazole derivatives of the general formula I. The simultaneous occurrence of an aminolysis of the carboxylic acid ester groups is avoided if necessary in the case of reactions with primary or secondary amines of the general formula III having lower radicals $R_2$ and $R_3$ by employing mild reaction conditions and/or only a slight excess of such amines, or by use of secondary amines in the form of their alkali metal derivatives.

Process (e) is performed by reacting, for example, a carboxylic acid of the general formula I e with a compound of the general formula VII in the presence of a carbodiimide, such as dicyclohexyl-carbodiimide, in an inert solvent such as tetrahydrofuran. Furthermore, a carboxylic acid of the general formula I e can be allowed to react with a lower alkylisocyanate or alkylthiocyanate—as reactive functional derivative of a compound of the general formula VII—and the immediate reaction product heated until evolution of carbon dioxide or carbon oxysulphide ceases.

Suitable reactive functional derivatives of carboxylic acids of the general formula I e are, for example, lower alkyl esters thereof, which can be reacted with compounds of the general formula VII in some cases even at room temperature or, where necessary, with heating and, if required, in a closed vessel, depending on the reactivity and boiling temperature of the employed compound of the general formula VII. As the reaction medium in this case it is possible to use, e.g., a lower alkanol such as methanol or ethanol, or another inert organic solvent such as tetrahydrofuran or dioxane, optionally together with an excess of the compound to be reacted of the general formula VII.

Further suitable reactive functional derivatives of carboxylic acids of the general formula I e are halides thereof, especially chlorides, particularly in the form of their hydrohalides, such as hydrochlorides. These are produced preferably directly before the subsequent reaction with the compounds of the general formula VII from the corresponding free carboxylic acids and suitable acid halides such as thionyl chloride, oxalyl chloride or phosphorus tribromide, and further reacted without purification. The carboxylic acid halides or their hydrohalides are reacted with compounds of the general formula VII, preferably in the presence of the at least equivalent or at least double-equivalent amount of an acid-binding agent, e.g. of a strong tertiary organic base such as triethylamine, N-ethyl-diisopropylamine, pyridine or s-collidine, which in excess can also serve as reaction medium, or in the presence of a corresponding excess of the compound of the general formula VII to be reacted, in the presence or absence of an inert organic solvent, such as dioxane, tetrahydrofuran, benzene or dimethylformamide, at a temperature of between about 0° C. and 100° C., or at the boiling temperature of the reaction medium in the case where this is lower. It is possible under analogous reaction conditions to react also mixed anhydrides of carboxylic acids of the general formula I e, especially the mixed anhydrides with carbonic acid semi-esters obtainable, e.g., by reaction of alkali metal salts of such carboxylic acids with chloroformic acid esters, preferably chloroformic acid lower alkyl esters, with compounds of the general formula VII.

Further suitable reactive functional derivatives of carboxylic acid esters of the general formula I e are, e.g., reactive esters such as p-nitrophenyl esters and cyanomethyl esters, which can be reacted with compounds of the general formula VII in inert organic solvents, if necessary with heating. There are reacted under the same conditions the 1imidazolides of carboxylic acids of the general formula I e with compounds of the general formula VII.

As reactive functional derivatives of compounds of the general formula VII, there have already been mentioned lower alkylisocyanates and lower alkylisothiocyanates which are derived from compounds of the general formula VII having a hydrogen atom as $R_5$. The reactions of these with carboxylic acids of the general formula I e can be performed in the presence or absence of an inert organic solvent having a sufficiently high boiling point or boiling range, e.g. toluene or xylene or an xylene mixture. Further reactive functional derivatives of compounds of the general formula VII having a hydrogen atom as $R_5$ are, e.g., the N-tri-(lower alkyl)-silyl derivatives obtainable by reaction of these compounds with tri-(lower alkyl)-silyl chlorides, such as trimethylsilyl chloride, in inert anhydrous organic solvents. The reaction thereof with reactive functional derivatives of carboxylic acids of the general formula I e in inert organic solvents yields N-tri-(lower alkyl)-silyl derivatives of carboxamides embraced by the general formula I, from which the desired carboxamides are liberated by decomposition with water or with lower alkanols.

Suitable functional derivatives of such compounds of the general formula VII in which neither $R_4$ nor $R_5$ represents hydrogen are, e.g., N-chlorocarbonyl derivatives thereof. These are reacted with salts, e.g. alkali metal salts of carboxylic acids of the general formula I e in the presence or absence of inert organic solvents, such as toluene or dimethylformamide, and the reaction mixtures are heated until the equimolar amount of carbon dioxide is liberated from the primarily formed carboxylic acid-carbamic acid-anhydrides. Likewise from compounds of the general formula VII wherein neither of the radicals $R_4$ and $R_5$ represents hydrogen are derived, e.g., sulphurous acid-monoalkyl estermonoamides, which yield, on reaction with carboxylic acids of the general formula I c in organic solvents, e.g. in pyridine, dioxane or dimethylformamide or in benzene, the desired carboxamides embraced by the general formula I.

Suitable reactive esters of compounds of the general formula I f are, for example, sulphonic acid esters thereof, particularly lower alkanesulphonic acid esters such as methanesulphonic acid esters, and arenesulphonic acid esters such as o- and p-toluenesulphonic acid esters, o- or p-nitrobenzenesulphonic acid esters or o- or p-chlorobenzenesulphonic acid esters. Further suitable reactive esters of compounds of the general formula I f are hydrohalic acid esters thereof, especially chlorides and bromides, as well as the iodides produced in situ therefrom. The reactions with compounds of the general formula VII or with their alkali metal derivatives can be performed analogously to Process (a).

The compounds of the general formula I f can be produced by various processes according to the invention, e.g. by Process (b) if $R_2$ and $R_3$ are to be methyl, and particularly by Process (g), and converted by methods known per se into reactive esters. A further production possibility for the organic sulphonic acid esters embraced also be the general formula VIII of the starting materials for Process (g) is given later on in the text.

In the starting materials of the general formula VIII for Process (g), the acyl radical Ac is preferably the acyl radical of a carboxylic acid, of a carbonic acid semi-ester or of an organic sulphonic acid. As an acyl radical of a carboxylic acid, Ac is, e.g., lower alkanoyl such as formyl, propionyl, butyryl, isobutyryl, valeryl or pivaloyl and, in particular, acetyl, also, e.g., halogenated lower alkanoyl such as trifluoroacetyl or trichloroacetyl, or arenecarbonyl such as benzoyl, p-chlorobenzoyl or p-nitrobenzoyl. As an acyl radical of a carbonic acid semi-ester, Ac is, e.g., methoxycarbonyl, ethoxycarbonyl, propoxycarbonyl, butoxycarbonyl, tert.-butoxycarbonyl, phenoxycarbonyl or benzyloxycarbonyl, and as an acyl radical of an organic sulphonic acid, it is, e.g., lower alkylsulphonyl such as methylsulphonyl, or arylsulphonyl such as phenylsulphonyl, o- or p-tolylsulphonyl, o- or p-nitrophenylsulphonyl or o- or p-chlorophenylsulphonyl. The solvolysis of compounds of the general formula VIII according to (g) can be performed by methods known per se in a basic or acid medium, for example in lower-alkanolic or lower-alkanolic-aqueous alkali hydroxide solutions, at room temperature up to the boiling temperature of the reaction mixture, or with aqueous or aqueous-organic mineral acids, e.g. in dilute hydrochloric acid, to which is optionally added a water-miscible organic solvent such as dioxane, tetrahydrofuran, methanol or ethanol, at the same temperatures.

The starting materials of the general formula VIII are obtained, for example, starting from compounds of the general formula I wherein $R_1$ is lower alkoxycarbonyl by simultaneous reduction of this group to the hydroxymethyl group and of the carbonyl group situated between the rings A and B to the hydroxymethylene group by means of a complex hydride, such as lithium aluminium hydride, in an ethereal solvent, such as tetrahydrofuran, at a temperature of between about 0° C. and room temperature, followed by partial acylation of the hydroxymethyl group by methods known per se; and finally oxidation of the hydroxymethylene group to the carbonyl group, analogously to the aforementioned Process (c) for the production of compounds of the general formula I.

For the oxidation of triazole derivatives of the general formula I h to triazole derivatives of the general formula I having formyl as $R_1$ according to Process (h), there are used mild selective oxidising agents, such as dimethylsulphoxide, optionally in the presence of a water-binding agent, such as dicyclohexylcarbodiimide and phosphoric acid, at room temperature or at moderately elevated temperatures up to about 100° C.; or manganese dioxide, which is preferably activated according to J. Attenburrow et al., *J. Chem. Soc.* 1952, 1104, in an inert organic solvent at a temperature of between about 50° C. and the boiling temperature of the solvent, e.g. in boiling benzene. The oxidising agent employed can also be chromium trioxide, e.g. dissolved in dilute sulphuric acid as an oxidation solution according to Jones, with this oxidation solution being slowly added, preferably at between 0° C. and room temperature, to the solution of the starting material in acetone. The starting materials of the general formula I h are produced for example, by the aforementioned Process (g) or, if $R_2$ and $R_3$ are methyl, also by Process (b).

Dehydration of the triazole derivatives of the general formula I i according to Process (i) can be performed, by methods known per se, at room temperature or at elevated temperatures up to about 180° C. For example, there is allowed to react with a carboxamide of the general formula I i an organic or inorganic acid halide, especially a sulphonic acid halide such as p-toluenesulphonyl chloride or methanesulphonyl chloride, or a halide of an acid of trivalent or pentavalent phosphorus, such as phosphorus oxychloride, or an acid anhydride, particularly the anhydride of an inorganic oxygen acid such as phosphorus pentoxide, in an inert organic solvent such dimethylformamide or xylene. The sulphonic acid halides, such as p-toluenesulphonyl chloride, are used preferably in an equimolar amount or in a moderate excess, optionally together with a somewhat greater excess of an acid-binding agent, especially of a tertiary organic base such as pyridine. Dehydration can for example be performed at room temperature, or if necessary at slightly elevated temperatures, by means of the approx. 1.5-fold molar amount of p-toluenesulphonyl chloride and the approx. 2-fold to 3-fold molar amount of pyridine in dimethylformamide. A further example of a dehydrating agent to be mentioned is triphenylphosphine, which can be caused to react, e.g., in a halogenated hydrocarbon, such as carbon tetrachloride, with a carboxamide of the general formula I i. The starting materials of the general formula I i can be produced by a number of the aforementioned processes, particularly by Process (e).

As alkali metal cyanide for process (j), there are used, for example, potassium cyanide and, in particular, sodium cyanide. By selective oxidising agents are meant those which do not under the reaction conditions attack the aldehyde group of the starting material of formula I j, but which are able to oxidise the hydroxymethylene group of the intermediately formed cyanohydrin to the carbonyl group. A suitable oxidising agent is manganese dioxide, particularly that in the active form described by J. Attenburrow et al., *J. Chem. Soc.* 1952, 1104. The reactions with manganese dioxide are preferably performed in isopropanol, or in another lower secondary alkanol, to which can be added a further organic solvent inert under the reaction conditions, preferably one having a good dissolving power for the starting materials of the general formula I j, such as for example dioxane, in the cold state, e.g. between −10° C. and +10° C., preferably at about 0° C. Relative to the compound of the general formula I j, there is used, for example, a considerable excess of the compound of the general formula VII, and also of alkali metal cyanide, e.g. the approx. 5-fold molar amount of the latter and an even greater excess, e.g. the approx. 20-fold molar amount, of manganese dioxide, with a reaction time of 2 to 6, preferably about 4, hours. The triazole derivatives of the general formula I J, used as starting materials, are produced, for example, by the aforementioned Process (h), and also by the Process (c) with the use of compounds of the general formula V in which $R_1$ represents a hydroxymethyl group.

The present invention relates also to such modifications of the processes mentioned under (a) to (j) and to the preliminary stages thereof, wherein a process is interrupted at some stage, or wherein a compound occurring as an intermediate at some stage is used as starting material and the uncompleted steps are performed, or wherein a starting material is formed under the reaction conditions, or, optionally, is used in the form of a salt. If the required starting materials are optically active, then both the racemates and the isolated antipodes can be used, or in the case of diasteriomeric compounds either mixtures of racemates or specific racemates, or likewise isolated antipodes can be used. Also such starting materials can, optionally, be used in the form of salts. The starting materials preferably employed for the carrying out of the reactions according to the invention are those from which are obtained the groups of final materials to which particular reference was made at the commencement of the text.

Depending on the conditions of the process and on the starting materials, the end products are obtained in the free form, or in the form, likewise included in the invention, of their acid addition salts, or in some cases in the form of hydrates of the last-mentioned. The acid addition salts of the new compounds of the general formula I can be converted in a known manner into the free bases, e.g. with basic agents, such as alkalies or ion exchangers. Alternatively, the compounds of the general formula I obtained by the process according to the invention can, optionally, be converted in the usual manner into their addition salts with inorganic or organic acids. For example, the acid desired as salt component is added to a solution of a compound of the general formula I in an organic solvent. Solvents preferably used for the reaction are those in which the ocurring salt is difficultly soluble, so that the salt can be separated by filtration. Such solvents are, for example, ethyl acetate, methanol, ether, acetone, methyl ethyl ketone, acetone/ether, acetone/ethanol, methanol/ether and ethanol/ether.

It is possible to use as pharmaceutic active substances, instead of free bases, pharmaceutically acceptable acid addition salts, i.e. salts with acids of which the anions are not toxic in the dosage amounts concerned. Moreover, it is of advantage if the salts to be used as pharmaceutical active substances readily crystallise, and are not, or only slightly, hygroscopic. For salt formation with compounds of the general formula I, it is possible to use, e.g., hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicyclic acid, phenylacetic acid, mandelic acid and embonic acid.

The new compounds can be present, depending on the choice of starting materials and working procedures, as optical antipodes or racemates or, if they have at least two asymmetric carbon atoms, also as mixtures of isomers (racemate mixtures). The mixtures of isomers (racemate mixtures) obtained can, by virtue of the physical-chemical differences in the constituents, be separated in a known manner into the two stereoisomeric (diastereomeric) pure racemates, e.g. by chromatography and/or fractional crystallisation.

Resulting racemates can be resolved by known methods, for example by recrystallisation from an optically active solvent, with the aid of microorganisms, or by reaction with an optically active acid forming salts with the racemic compound, and separation of the salts obtained in this manner, e.g. by virtue of their different degrees of solubility, into the diastereomers from which the antipodes can be liberated by the action of suitable agents. Particularly suitable optically active acids are, for example, the D- and L-forms of tartaric acid, di-o-toluyltartaric acid, malic acid, mandelic acid, camphorsulphonic acid or quinic acid. It is of advantage to isolate the more effective of the two antipodes.

The new compounds are administered orally, rectally or parenterally. The dosage amount depends on the mode of administration, on the species, on the age and on the individual condition. The daily doses of the free bases or of pharmaceutically acceptable salts thereof vary between 0.1 mg/kg and 3 mg/kg for warm-blooded animals. Suitable dosage units, such as dragées, tablets, suppositories or ampoules, preferably contain 0.5–50 mg of an active substance according to the invention.

Dosage units for oral administration contain as active substance preferably between 0.5 and 50% of a compound of the general formula I, or of a pharmaceutically acceptable salt thereof. The said dosage units are produced by combination of the active substance with, e.g., solid pulverulent carriers such as lactose, saccharose, sorbitol or mannitol; starches such as potato starch, maize starch or amylopectin, also laminaria powder or citrus pulp powder, cellulose derivatives or gelatine, optionally with the addition of lubricants, such as magnesium or calicum stearate or polyethylene glycols, to form tablets or dragée cores. The dragée cores are coated, for example, with concentrated sugar solutions which can also contain, e.g., gum arabic, talcum and/or titanium dioxide, or with a lacquer dissolved in readily volatile organic solvents or solvent mixtures. Dyestuffs may be added to these coatings, e.g. for identification of the various dosage amounts.

Further suitable oral dosage units are hard gelatine capsules, as well as soft closed capsules made from gelatine and a softener such as glycerin. The hard gelatine capsules contain the active substance preferably as a granulate, e.g. in admixture with fillers such as maize starch, and/or lubricants such as talcum or magnesium stearate, and optionally stabilisers such as sodium metabisulphite ($Na_2S_2O_5$) or ascorbic acid. In soft capsules, the active substance is preferably dissolved or suspended in suitable liquids, such as in polyethylene glycols, to which likewise stabilisers may be added.

Suitable dosage units for rectal administration are, e.g., suppositories consisting of a combination of an active substance with a suppository foundation substance. Applicable suppository foundation substances are, e.g., natural or synthetic triglycerides, paraffin hydrocarbons, polyethylene glycols or higher alkanols. Also suitable are gelatine rectal capsules consisting of a combination of the active substance with a foundation substance. Suitable foundation substances are, e.g., liquid triglycerides, polyethylene glycols or paraffin hydrocarbons.

Ampoules for parenteral administration, especially intramuscular administration, preferably contain a water-soluble salt of an active substance in a concentration preferably of 0.2–5%, optionally together with suitable stabilisers and buffer substances, in aqueous solution.

The following working examples further illustrate the production of tablet, dragées, supositories and ampoules:

(a) 50.0 g of N-propyl-1-[2-(o-chlorobenzyl)-4-chlorophenyl]-5-[(dimethylamino)-methyl]-1H-1,2,4-triazole-3-carboxamide is mixed with 500 g of lactose and 292 g of potato starch; the mixture is moistened with an alcoholic solution of 8 g of gelatine, and then granulated through a sieve. After drying of the granulate 60 g of potato starch, 60 g of talcum, 10 g of magnesium stearate and 20 g of highly dispersed silicon dioxide are mixed in, and the mixture is subsequently pressed out to form 10,000 tablets each weighing 100.0 mg and each containing 5.0 mg of active substance; the tablets can be provided with grooves to effect a more precise adjustment of the dosage amount.

(b) 2.50 g of N-ethyl-1-[2-(o-chlorobenzoyl)-4-chlorophenyl]-5-(dimethylamino)-methyl]-1H-1,2,4-triazole-3-carboxamide is well mixed with 16 g of maize starch and 6 g of highly dispersed silicon dioxide. The mixture is moistened with a solution of 2 g of stearic acid, 6 g of ethylcellulose and 6 g of stearin in about 70 ml of isopropyl alcohol, and is then granulated through a sieve III (Ph.Helv. V). The granulate is dried for about 14 hours and is subsequently put through sieve III-IIIa. It is then mixed with 16 g of maize starch, 16 g of talcum and 2 g of magnesium stearate and the mixture is pressed out to form 1000 dragée cores. These are coated with a concentrated syrup of 2 g of lacca, 7.5 g of gum arabic, 0.15 g of dyestuff, 2 g of highly dispersed silicon dioxide, 25 g of talcum and 53.35 g of sugar, and finally dried. The dragées obtained each weight 162.5 mg and each contain 2.5 mg of active substance.

(c) 10.0 g of 1-[2-(o-chlorobenzoyl)-4-chlorophenyl]-5-(morpholinomethyl)-1H-1,2,4-triazolo-3-carboxamide and 1990 g of finely ground suppository foundation substance (e.g. cocoa butter) are thoroughly mixed and then melted. From the melt, maintained homogeneous by stirring, there are formed 1000 suppositories each weighing 2 g and each containing 10 mg of active substance.

(d) A solution of 5.0 g of 1-[2-(o-chlorobenzoyl)-4-chlorophenyl]-3,5-bis-[(dimethylamino)-methyl]-1H-1,2,4-triazole-dihydrochloride in one liter of water is filled into 1000 ampoules and sterilised. Each ampoule contains 5 mg of active substance as a 0.5% solution.

The following examples further illustrate the production of the new compounds of the general formula I as well as of starting materials not hitherto known, but they are not intended to limit in any way the scope of the invention. Temperatures are given in degrees Centigrade.

EXAMPLE 1

A mixture of 8.8 g (0.018 mole) of 1-(2-benzoyl-4-chlorophenyl)-5-(iodomethyl)-1H-1,2,4-triazole-3-carboxylic acid methyl ester and 3.5 ml (0.040 mole) of morpholine are stirred in 175 ml of methanol at 40° for 6 hours. The reaction mixture is thereupon concenentrated in vacuo, water is added to the residue, and extraction is performed twice with methylene chloride. The organic phase is washed three times with water and once with saturated sodium chloride solution; it is dried over sodium sulphate and concentrated in vacuo. The residue is triturated with ether, whereupon the reaction product is obtained in crystalline form. After filtration with suction and drying in vacuo, there is obtained 1-(2-benzoyl-4-chlorophenyl)-5-(morpholinomethyl)-1H-1,2,4-triazole-3-carboxylic acid methyl ester, m.p. 165°–170°.

The starting material is produced as follows:

(a) 224 ml of a 6N solution of hydrogen chloride in methanol is added to a solution of 112.2 g (0.299 mole) of 1-(2-benzoyl-4-chlorophenyl)-5-(chloromethyl)-1H-1,2,4-triazole-3-carboxylic acid in 1120 ml of methanol, and the whole is refluxed for 21 hours. There is then distilled off 800 ml of methanol at normal pressure, and the concentrated solution is allowed to stand for 18 hours at room temperature. The product that has crystallised out is filtered off under suction and washed with cold methanol and hexane. After drying in vacuo, there is obtained 1-(2-benzoyl-4-chlorophenyl)-5-(chloromethyl)-1H-1,2,4-triazole-3-carboxylic acid methyl ester, m.p. 132°–134°.

(b) A solution of 51.6 g (0.132 mole) of 1-(2-benzoyl-4-chlorophenyl)-5-(chloromethyl)-1H-1,2,4-triazole-3-carboxylic acid methyl ester and 29.8 g (0.198 mole) of sodium iodide in 1000 ml of acetone is refluxed for 45 minutes. The reaction mixture is thereupon concentrated in vacuo. Water is added to the residue and extraction is performed twice with methylene chloride. The organic phase is washed once with diluted aqueous sodium bisulphite solution and twice with saturated sodium chloride solution; it is dried over sodium sulphate and concentrated in vacuo. The residue is triturated with ether, whereupon the reaction product crystallises out. After filtration under suction and drying in vacuo, there is obtained 1-(2-benozyl-4-chlorophenyl)-5-(iodomethyl)-1H-1,2,4-triazole-3-carboxylic acid methyl ester, m.p. 139°–142°.

EXAMPLE 2

A mixture of 24.0 g (0.050 mole) of 1-(2-benzoyl-4-chlorophenyl)-5-(iodomethyl)-1H-1,2,4-triazole-3-carboxylic acid methyl ester [see Example 1a) and b)] and 20.5 ml of 33% ethanolic dimethylamine solution in 480 ml of methanol is stirred for 2 hours at room temperature. The reaction solution is thereupon concentrated in vacuo; water is added to the residue and extraction is performed twice with methylene chloride. The organic phase is washed twice with water and once with saturated sodium chloride solution; it is dried over sodium sulphate and concentrated in vacuo to dryness. The amorphous residue is dissolved in 150 ml of ether. The reaction product crystallises out whilst the solution is allowed to stand. The reaction product is filtered off under suction and washed with ether. After drying, there is obtained 1-(2-benzoyl-4-chlorophenyl)-5-[(dimethylamino)-methyl]-1H-1,2,4-triazole-3-carboxylic acid methyl ester, m.p. 118°–121°.

EXAMPLE 3

To the solution of 6.0 g (0.0203 mole) of 6-phenyl-8-chloro-4H-s-triazolo[1,5-a][1,4]benzodiazepine (see German 'Offenlegungsschrift' No. 2,159,527) in 27 ml of 85% formic acid there is added 13.7 ml of 36% aqueous formaldehyde solution, and the mixture is heated, with stirring, for 2 hours at 100°. The reaction solution is then allowed to cool to room temperature; it is poured into ice water, and concentrated sodium hydroxide solution is added until the pH-value has reached 11. The precipitated crude product is taken up in ether. The organic phase is washed twice with water and once with saturated sodium chloride solution; it is dried over sodium sulphate and concentrated in vacuo. The residue is dissolved in 100 ml of ethyl acetate, and ethereal hydrochloric acid solution is added until the pH have reached a value of 3. The hydrochloride precipitates out in crystalline form. It is filtered off with suction after 2 hours and washed with ether and hexane. There is obtained 1-(2-benzoyl-4-chlorophenyl)-5-[(dimethylamino)-methyl]-1H-1,2,4-triazole hydrochloride, m.p. 182°–185° with decomposition.

EXAMPLE 4

13.5 ml of 85% formic acid and 6.7 ml of 36% aqueous formaldehyde solution are added to 3.4 g (0.001 mole) of 6-phenyl-8-chloro-4H-s-triazolo[1,5-a][1,4]benzodiazepine-2-carboxylic acid (see German 'Offenlegungsschriften' Nos. 2,159,527 and 2,215,943). The reaction mixture is subsequently heated, with stirring, at 100° for 2 hours, in which time the starting product goes completely into solution. After cooling, there is added concentrated sodium hydroxide solution until the pH has reached a value of 5, and the mixture is concentrated in vacuo to dryness. In order to obtain complete drying, the residue is concentrated a further three times with a mixture of toluene/methanol (1:1) in vacuo at 60°. The residue is extracted three times with boiling methylene chloride. The organic phase is concentrated in vacuo, and the residue is dissolved in 300 ml of ethyl acetate. The cloudy solution is treated with charcoal and filtered through Hyflo. A solution of hydrogen chloride in ether is added to the clear filtrate until an acid reaction to Congo red is indicated. The precipitated crystals are filtered with suction and washed with ethyl acetate and ether. There is obtained 1-(2-benzoyl-4-chlorophenyl)-5-[(dimethylamino)-methyl]-1H-1,2,4-triazole-3-carboxylic acid hydrochloride, m.p. 160°–165° with decomposition.

The following are obtained in an analogous manner: from 3.25 g (0.001 mole) of 6-phenyl-8-chloro-4H-s-triazolo[1,5-a][1,4]benzodiazepine-2-methanol: 1-(2-benzoyl-4-chlorophenyl)-5-[(dimethylamino)-methyl]-1H-1,2,4-triazole-3-methanol-hydrochloride; from 3.43 g (0.001 mole) of 6-(o-fluorophenyl)-8-chloro-4H-s-triazolo[1,5-a][1,4]benzodiazepine-2-methanol: 1-[2-(o-fluorobenzoyl)-4-chlorophenyl]-5-[(dimethylamino)-methyl]-1H-1,2,4-triazole-3-methanol-hydrochloride; and from 3.59 g (0.001 mole) of 6-(o-chlorophenyl)-8-chloro-4H-s-triazolo[1,5-a][1,4]benzodiazepine-2-methanol: 1-[2-(o-chlorobenzoyl)-4-chlorophenyl]-5-[(dimethylamino)-methyl]-1,2,4-triazole-3-methanol-hydrochloride.

The production of the starting materials is described in the German 'Offenlegungsschrift' No. 2,234,652.

EXAMPLE 5

35 ml of 36% aqueous formaldehyde solution is added to the solution of 19.2 g (0.050 mole) of N,N-dimethyl-6-(o-fluorophenyl)-8-chloro-4H-s-triazolo[1,5-a][1,4]benzodiazepine-2-carboxamide (see German 'Offenlegungsschrift' No. 2,304,307) in 68 ml of 85% formic acid, and the mixture is heated with stirring for 2 hours at 100°. The reaction mixture is afterwards cooled to room temperature; it is poured into ice water, and concentrated sodium hydroxide solution is added until the pH-value reaches 11. The precipitated crude product is taken up in methylene chloride. The methylene chloride solution is washed twice with water and once with saturated sodium chloride solution; it is dried over sodium sulphate and concentrated in vacuo. The residue is recrystallised from isopropanol and, after drying in vacuo, there is obtained N,N-dimethyl-1-[2-(o-fluorobenzoyl)-4-chlorophenyl]-5-[(dimethylamino)-methyl]-1H-1,2,4-triazole-3-carboxamide, m.p. 140°–142°.

The following are obtained in an analogous manner:
from 20.6 g of N,N-diethyl-6-(o-fluorophenyl)-8-chloro-4H-s-triazolo[1,5-a][1,4]benzodiazepine-2-carboxamide: N,N-diethyl-1-[2-(o-fluorobenzoyl)-4-chlorophenyl]-5-[(dimethylamino)-methyl]-1H-1,2,4-triazole-3-carboxamide;

from 20.0 g of N,N-dimethyl-6-(o-chlorophenyl)-8-chloro-4H-s-triazolo[1,5-a][1,4]benzodiazepine-2-carboxamide: N,N-dimethyl-1-[2-(o-chlorobenzoyl)-4-chlorophenyl]-5-[(dimethylamino)-methyl]-1H-1,2,4-triazole-3-carboxamide, m.p. 144°–145°;

from 21.4 g of N,N-diethyl-6-(o-chlorophenyl)-8-chloro-4H-s-triazolo[1,5-a][1,4]benzodiazepine-2-carboxamide: N,N-diethyl-1-[2-(o-chlorobenzoyl)-4-chlorophenyl]-5-[(dimethylamino)-methyl]-1H-1,2,4-triazole-3-carboxamide, the melting point of the oxalate to 115°–118°;

from 18.3 g of N,N-dimethyl-6-phenyl-8-chloro-4H-s-triazolo[1,5-a][1,4]benzodiazepine-2-carboxamide: N,N-dimethyl-1-(2-benzoyl-4-chlorophenyl)-5-[(dimethylamino)-methyl]-1H-1,2,4-triazole-3-carboxamide, from 19.7 g of N,N-diethyl-6-phenyl-8-chloro-4H-s-triazolo[1,5a][1,4]benzodiazepine-2-carboxamide: N,N-diethyl-1-(2-benzoyl-4-chlorophenyl)-5-[(dimethylamino)-methyl]-1H-1,2,4-triazole-3-carboxamide, m.p. 118°–120°;

from 20.0 g of N,N-dimethyl-6-phenyl-8-(trifluoromethyl)-4H-s-triazolo[1,5-a][1,4]benzodiazepine-2-carboxamide: N,N-dimethyl-1-(2-benzoyl-α,α,α-trifluoro-p-tolyl)-5-[(dimethylamino)-methyl]-1H-1,2,4-triazole-3-carboxamide;

from 18.8 g of N,N-dimethyl-6-phenyl-8-nitro-4H-s-triazolo[1,5-a][1,4]benzodiazepine-2-carboxamide: N,N-dimethyl-1-(2-benzoyl-4-nitrophenyl)-5-[(dimethylamino)-methyl]-1H-1,2,4-triazole-3-carboxamide;

from 19.7 g of N,N-dimethyl-6(o-fluorophenyl)-8-nitro-4H-s-triazolo[1,5-a][1,4]benzodiazepine-2-carboxamide:

N,N-dimethyl-1-[2-(o-fluorobenzoyl)-4-nitro-
phenyl]-5-[(dimethylamino)-methyl]-1H-1,2,4-
triazole-3-carboxamide;

from 16.9 g of 6-phenyl-8-chloro-4H-s-triazolo[1,5-
a][1,4]benzodiazepine-2-carboxamide: 1-(2-benz-
oyl-4-chlorophenyl)-5-[(dimethylamino)-methyl]-
1H-1,2,4-triazole-3-carboxamide;

from 18.6 g of 6-(o-chlorophenyl)-8-chloro-4H-s-
triazolo[1,5-a][1,4]benzodiazepine-2-carboxamide:
1[2-(o-chlorobenzoyl)-4-chlorophenyl]-5-[(dime-
thylamino)-methyl]-1H-1,2,4-triazole-3-carboxa-
mide;

from 17.8 g of 6-(o-fluorophenyl)-8-chloro-4H-s-
triazolo[1,5-a][1,4]benzodiazepine-2-carboxamide:
1-[2-(o-fluorobenzoyl)-4-chlorophenyl]-5-[(dime-
thylamino)-methyl]-1H-1,2,4-triazole-3-carboxa-
mide;

from 18.5 g of N-methyl-6-(o-fluorophenyl)-8-chloro-
4H-s-triazolo[1,5a-][1,4]benzodiazepine-2-carboxa-
mide:
N-methyl-1-[2-(o-fluorobenzoyl)-4-chlorophenyl]-
5-[(dimethylamino)-methyl]-1H-1,2,4-triazole-3-
carboxamide;

from 19.3 g of N-methyl-6-(o-chlorophenyl)-8-
chloro-4H-s-triazolo[1,5-a][1,4]benzodiazepine-2-
carboxamide:
N-methyl-1-[2-(o-chlorobenzoyl)-4-chlorophenyl]-
5-[(dimethylamino)-methyl]-1H-1,2,4-triazole-
3carboxamide; m.p. 155°-158°;

from 19.2 g of N-ethyl-6-(o-fluorophenyl)-8-chloro-
4H-s-triazolo[1,5-a][1,4]benzodiazepine-2-carboxa-
mide:
N-ethyl-1-[2-(o-fluorobenzoyl)-4-chlorophenyl]-5-
[(dimethylamino)-methyl]-1H-1,2,4-triazole-3-
carboxamide;

from 19.9 g of N-isopropyl-6-(o-fluorophenyl)-8-
chloro-4H-s-triazole[1,5-a][1,4]benzodiazepine-2-
carboxamide:
N-isopropyl-1-[2-(o-fluorobenzoyl)-4-chloro-
phenyl]-5-[(dimethylamino)-methyl]-1H-1,2,4-
triazole-3-carboxamide;

from 21.3 g of 4[[6-(o-fluorophenyl)-8-chloro-4H-s-
triazolo[1,5a-][1,4]benzodiazepin-2-yl]-carbonyl]-
morpholine: 4-[[1-[2-(o-fluorobenzoyl)-4-chloro-
phenyl]-5-[(dimethylamino)-methyl]-1H-1,2,4-
triazol-3-yl]-carbonyl]-morpholine;

from 20.5 g of 1-[[6-(o-fluorophenyl)-8-chloro-4H-s-
triazolo[1,5-a][1,4]benzodiazepin-2-yl]-carbonyl]-
pyrrolidine: 1-[[1-[2-(o-fluorobenzoyl)-4-chloro-
phenyl]-5-[(dimethylamino)-1H-1,2,4-
triazol-3-yl]-carbonyl]-pyrrolidine;

from 21.2 g of 1-[[6-(o-fluorophenyl)-8-chloro-4H-s-
triazolo[1,5-a][1,4]benzodiazepin-2-yl]-carbonyl]-
piperidine: 1-[[1-[2-(o-fluorobenzoyl)-4-chloro-
phenyl]-5-[(dimethylamino)-methyl]-1H-1,2,4-
triazol-3-yl]-carbonyl]-piperidine;

from the base liberated from 23.8 g (0.050 mole) of
1-[[6-(o-fluorophenyl)-8-chloro-4H-s-triazolo[1,5-
a][1,4]benzodiazepin-2-yl]-carbonyl]-4-methylpip-
erazine hydrochloride: -1-[[1-[2-(o-fluorobenzoyl)-
4-chlorophenyl]-5-[(dimethylamino)-methyl]-1H-
1,2,4-triazol-3-yl]-carbonyl]-4-methylpiperazine
and the dihydrochloride thereof.

The starting materials used are described in the German 'Offenlegungsschrift' No. 2,304,307.

EXAMPLE 6

8.35 ml (about 0.10 mole) of 36% aqueous formaldehyde solution is added to the solution of the base, liberated from 4.30 g (0.010 mole) of 2-[(methylamino)-methyl]-6-(o-chlorophenyl)-8-chloro-4H-s-triazolo[1,5-a][1,4]benzodiazepine-fumarate-(2:1) (see German 'Offenlegungsschrift' No. 2,234,652), in 13.5 ml (about 0.25 mole) of 85% formic acid, and the mixture is heated, with stirring, for 2 hours at 100°. The reaction solution is afterwards cooled to room temperature; it is poured into ice water, and concentrated sodium hydroxide solution is added until the pH-value has reached 11. The crude product that has precipitated is taken up in ether. The organic phase is washed twice with water and once with saturated sodium chloride solution; it is dried over sodium sulphate and then concentrated in vacuo. The oily residue is dissolved in 100 ml of ethanol, and ethereal hydrogen chloride solution is added until the pH-value has reached 2. The ethanol is thereupon completely distilled off in vacuo, and ethyl acetate is added to the residue. The product obtained in crystalline form is filtered with suction and washed with ethyl acetate and ether. After drying in vacuum, there is obtained 1-[2-(o-chlorobenzoyl)-4-chlorophenyl]-3,5-bis-(dimethyl amino)-methyl]-1H-1,2,4-triazole-dihydrochloride, m.p. 100°-105° with decomposition.

The following are obtained in an analogous manner: from the base liberated from 4.30 g (0.010 mole) of 2-[(methylamino)-methyl]-6-(o-fluorophenyl)-S-chloro-4H-s-triazolo[1,5-a][1,4]benzodiazepine-hydrochloride-dihydrate:
1-[2-(o-fluorobenzoyl)-4-chlorophenyl]-3,5-bis-
[(dimethylamino)-methyl]-1H-1,2,4-triazole and
the dihydrochloride thereof.

The following are obtained likewise analogously but, if desired, with reduction of the amount of 36% formaldehyde solution to 5.85 ml (about 0.07 mole):

from 3.52 g (0.010 mole) of 2-[(dimethylamono)-
methyl]-6-phenyl-8-chloro-4H-s-triazolo[1,5-
a][1,4]benzodiazepine:
1-(2-benzoyl-4-chlorophenyl)-3,5-bis-[(dime-
thylamine)methyl]-1H-1,2,4-triazole and the di-
hydrochloride thereof;

from 3.92 g (0.010 mole) of 2-(piperidinomethyl)-6-
phenyl-8-chloro-4H-s-triazolo[1,5-a][1,4]ben-
zodiazepine:
1-(2-benzoyl-4-chlorophenyl)-3-(piperidineme-
thyl)-5-[(dimethylamine)-methyl]-1H-1,2,4-
triazole and the dihydrochloride thereof;

from 3.78 g (0.010 mole) of 2-[(1-pyrrolidinyl)-
methyl]-6-phenyl-8-chloro-4H-s-triazolo[1,5-
a][1,4]benzodiazepine:
1-(2-benzoyl-4-chlorophenyl)-3,-[(1-pyrrolidinyl)-
methyl]-5-[(dimethylamino)-methyl]-1H-1,2,4-
triazole and the dihydrochloride thereof;

from 3 94 g (0.010 mole) of 2-(morpholinomethyl)-6-
phenyl-8-chloro-4H-s-triazolo[1,5-a][1,4]ben-
zodiazepine:
1-(2-benzoyl-4-chlorophenyl)-3-(morpholinome-
thyl)-5-[(dimethylamino)-methyl]-1H-1,2,4-
triazole and the dihydrochloride thereof; and from 4.07 g (0.010 mole) of 2-[(4-methyl-1-
piperazinyl)-methyl]-6-phenyl-8-chloro-4H-s-
triazolo[1,5-a][1,4]benzodiazepine:- 1-(2-benzoyl-4-
chlorophenyl)-3-[(4-methyl-1-piperazinyl)-
methyl]-5-[(dimethylamino)-methyl]-1H-1,2,4-
triazole and the trihydrochloride thereof.

The starting materials used are described in the German 'Offenlegungsschrift' No. 2,234,652.

EXAMPLE 7

7.6 g (0.017 mole) of 1-(2-benzoyl-4-chlorophenyl)-5-(morpholinomethyl)-1H-1,2,4-triazole-3-carboxylic acid methyl ester (see Example 1) is covered over with 340 ml of methanol and 69 ml of concentrated aqueous ammonia solution. The mixture is heated, with stirring, for 4 hours at 40°, with the starting material slowly going into solution. The reaction mixture is then allowed to stand for 18 hours at room temperature, and subsequently concentrated in vacuo. Water is added to the residue and extraction is performed twice with methylene chloride. The organic phase is washed twice with ice-cold 1N sodium bicarbonate solution, once with water and once with saturated sodium chloride solution; it is dried over sodium sulphate and then concentrated in vacuo to dryness. The residue is recrystallised from isopropanol to obtain, after drying in vacuum, 1-(2-benzoyl-4-chlorophenyl)-5-(morpholinomethyl)-1H-1,2,4-triazole-3-carboxamide, m.p. 146°–149°.

EXAMPLE 8

17.5 g (0.044 mole) of 1-(2-benzoyl-4-chlorophenyl)-5-[(dimethylamino)-methyl]-1H-1,2,4-triazole-3-carboxylic acid methyl ester (see Example 2) is covered over with 850 ml of methanol and 175 ml of concentrated aqueous ammonia solution. The reaction solution is stirred for 7 hours at room temperature, and afterwards concentrated in vacuo to dryness. Water is added to the residue, and extraction is performed twice with methylene chloride. The organic phase is washed twice with water and once with saturated sodium chloride solution; it is dried over sodium sulphate and concentrated in vacuo to dryness. The residue is dissolved in 300 ml of ethyl acetate, and ethereal hydrogen chloride solution is added until the pH-value has reached 2. The crystalline product is filtered with suction and washed with ethyl acetate and ether. After drying in vacuum, there is obtained 1-(2-benzoyl-4-chlorophenyl)-5-[(dimethylamino)-methyl]-1H-1,2,4-triazole-3-carboxamide-hydrochloride, m.p. 250–255° with decomposition.

EXAMPLE 9

9.00 g (0.018 mole) of crude 1-[2-(o-chlorobenzoyl)-4-chlorophenyl]-5-(morpholinomethyl)-1H-1,2,4-triazole-3-carboxylic acid hydrochloride is refluxed with 90 ml of thionyl chloride for 90 minutes. The clear solution is concentrated in vacuo at 40°, and the residue, in order to completely remove the thionyl chloride therefrom, is dissolved in 100 ml of absolute toluene and again concentrated by evaporation.

The crude acid chloride hydrochloride is covered over with 90 ml of concentrated aqueous ammonia solution and the whole is stirred for 18 hours at room temperature. The reaction mixture is afterwards cooled for 2 hours with ice water; the precipitated crude product is filtered off, and then well washed with cold water. After recrystallisation from isopropanol there is obtained 1-[2-(o-chlorobenzoyl)-4-chlorophenyl]-5-(morpholinomethyl)-1H-1,2,4-triazole-3-carboxamide, m.p. 165°–167°.

The starting material is produced as follows:

(a) 0.10 g of sodium iodide is added to a mixture of 9.3 g (0.0226 mole) of 1-[2-(o-chlorobenzoyl)-4-chlorophenyl]-5-(chloromethyl)-1H-1,2,4-triazole-3-carboxylic acid (see German 'Offenlegungsschrift' No. 2,159,527, page 32) and 9.5 g (0.11 mole) of morpholine in 100 ml of ethanol, and the whole is reflux for 2 hours. The reaction mixture is thereupon concentrated in vacuo; the residue is dissolved in water, and 2N hydrochloric acid is added until an acid reaction to Congo red is obtained. The precipitated hydrochloride of the reaction product is extracted twice with 100 ml of methylene chloride each time. After washing with saturated sodium chloride solution, drying over sodium sulphate and concentration by evaporation, the organic extracts yield 1-[2-(o-chlorobenzoyl)-4-chlorophenyl]-5-(morpholinomethyl)-1H-1,2,4-triazole-3-carboxylic acid hydrochloride in the form of an amorphous yellow foam, which is used directly for the next step.

EXAMPLE 10

The following are obtained analogously to Example 7: starting with 7.3 g (about 0.017 mole) of crude 1-(2-benzoyl-4-chlorophenyl)-5-[(1-pyrrolidinyl)-methyl]-1H-1,2,4-triazole-3-carboxylic acid methyl ester:- amorphous 1-(2-benzoyl-4-chlorophenyl)-5-[(1-pyrrolidinyl)-methyl]-1H-1,2,4-triazole-3-carboxamide, of which the hydrochloride, prepared with ethereal hydrogen chloride solution in ethyl acetate, melts at 236° (with decomposition) after recrystallisation from isopropanol; and starting with 7.5 g (about 0.017 mole) of crude 1-(2-benzoyl-4-chlorophenyl)-5-(piperidinomethyl)-1H-1,2,4-triazole-3-carboxylic acid methyl ester:- crude 1-(2-benzoyl-4-chlorophenyl)-5-(piperidinomethyl)-1H-1,2,4-triazole-3-carboxamide, of which the analogously prepared hydrochloride melts at 255°–260° (with decomposition) after recrystallisation from isopropanol.

The starting materials are produced as follows:

(a) By a procedure analogous to that of Example 1 there are obtained, with the use of 2.9 g (0.041 mole) of pyrrolidine and 3.0 g (0.041 mole) of piperidine, instead of morpholine, crude 1-(2-benzoyl-4-chlorophenyl)-5-[(1-pyrrolidinyl)-methyl]-1H-1,2,4-triazole-3-carboxylic acid methyl ester and crude 1-(2-benzoyl-4-chlorophenyl)-5-(piperidinomethyl)-1H-1,2,4-triazole-3-carboxylic acid methyl ester, respectively.

EXAMPLE 11

7.0 g (0.0165 mole) of crude 1-(2-benzoyl-4-nitrophenyl)-5-[(dimethylamino)-methyl]-1H-1,2,4-triazole-3-carboxylic acid ethyl ester (see below) is covered over with 200 ml of ethanol and 20 ml of concentrated aqueous ammonia solution. The reation mixture is allowed to stand for 3 days at room temperature, and is then concentrated in vacuo. Water is added to the residue and extraction is performed twice with ethyl acetate. The organic phase is washed twice with cold 1N sodium bicarbonate solution and twice with saturated sodium chloride solution; it is dried over sodium sulphate and concentrated in vacuo to dryness. The residue is dissolved in ethyl acetate/isopropanol (5:1), and the solution is chromatographed on a column of 150 g of silica gel. The eluting agent employed is ethyl acetate/isopropanol (5:1). The fractions containing the desired product are combined, and concentrated by evaporation. The residue is recrystallised from ethanol to obtain, after drying in vacuum, 1-(2-benzoyl-4-nitrophenyl)-5-[(dimethylamine)-methyl]-1H-1,2,4-triazole-3-carboxamide, m.p. 187°–190°.

There is obtained in an analogous manner, with the use of 7.3 g (0.0165 mole) of crude 1-[2-(o-fluorobenzoyl)- 4- nitrophenyl]-5-[(dimethylamino)-methyl]-1H-1,2,4-triazole-3-carboxylic acid ethyl ester (see below): 1-[2-(o-fluorobenzoyl)-4-nitrophenyl]-5-[(dimethylamino)-methyl]-1H-1,2,4-triazole-3-carboxamide.

The starting materials are produced as follows:

6 ml (0.072 mole) of 36% aqueous formaldehyde solution is added to the solution of 7.55 g (0.020 mole) of 6-phenyl-8-nitro-4H-s-triazolo[1,5-a][1,4]benzodiazepine-2-carboxylic acid ethyl ester (see German 'Offenlegungsschrift' No. ,304,307) in 50 ml of 85% formic acid, and the mixture is heated for 2 hours at 100°. The reaction mixture is afterwards poured into 200 ml of ice water, and an undissolved yellow by-product is separated by filtration through purified diatomaceous earth. Sodium carbonate is added to the filtrate, with ice cooling, until the pH-value has reached 9, and extraction is performed twice with ethyl acetate. The organic phase is washed twice with water and once with saturated sodium chloride solution; it is dried over sodium sulphate and concentrated in vacuo. The residue contains 1-(2-benzoyl-4-nitrophenyl)-5-[(dimethylamino)-methyl]-1H-1,2,4-triazole-3-carboxylic acid ethyl ester as viscous oil, which is used directly for ammonolysis.

There is obtained in an analogous manner, starting with 7.91 g (0.020 mole) of 6-(o-fluorophenyl)-8-nitro-4H-s-triazolo[1,5-a][1,4]benzodiazephine-2-carboxylic acid ethyl ester, described in the same 'Offenlegungsschrift', 1-[2-(o-fluorobenzoyl)-4- nitrophenyl)-5-[(dimethylamino)-methyl]-1H-1,2,4- triazole-3-carboxylic acid ethyl ester.

EXAMPLE 12

4.0 ml of 33% ethanolic dimethylamine solution is added to a mixture of 3.75 g (0.01 mole) of 1-(2-benzoyl-4-chlorophenyl)-5-(chloromethyl)-1H-1,2,4-triazole-3-carboxamide and 0.15 g of sodium iodide in 70 ml of methanol, and the whole is refluxed for 4 hours with stirring. The reaction mixture is subsequently concentrated in vacuo. Water and saturated sodium carbonate solution are added until the pH-value has reached 10, and extraction is performed twice with ethyl acetate. The organic phase is washed twice with water and once with saturated sodium chloride solution; it is then dried over magnesium sulphate and filtered. To the filtrate there is added ethereal hydrogen chloride solution until the pH-value has reached 3. The product precipitating in crystalline form is filtered off with suction and washed with ethyl acetate and ether. After drying in vacuum, there is obtained 1-(2-benzoyl-4-chlorophenyl)-5-[(dimethylamino)-methyl]-1H-1,2,4-triazole-3-carboxamide-hydrochloride, m.p. 250° with decomposition.

The starting material is produced as follows:
(a) 30 ml of concentrated aqueous ammonia solution is added dropwise at 30° in the course of 5 minutes, with stirring, to the suspension of 6.0 g (0.015 mole) of 1-(2-benzoyl-4-chlorophenyl)-5-(chloromethyl)-1H-1,2,4-triazole-3-carboxylic acid methyl ester in 220 ml of methanol. There has formed after 4 hours a clear reaction solution, and a short time later a crystalline product commences to precipitate. Stirring is maintained for one hour at room temperature and for one hour at 0°-5°. The formed crystals are thereupon filtered off and recrystallised from 50 ml of methanol. The product is filtered off with suction and washed with methanol and hexane. After drying in vacuum, there is obtained 1-(2-benzoyl-4-chlorophenyl)-5-(chloromethyl)-1H-1,2,4-triazole-3-carboxamide, m.p. 128°-130°.

EXAMPLE 13

A mixture of 38.7 g (0.075 mole) of 1-[2-(o-chlorobenzoyl)-4-chlorophenyl]-5-(iodomethyl)-1H-1,2,4-triazole-3-carboxylic acid methyl ester and 13.1 g (0.150 mole) of morpholine in 750 ml of methanol is stirred for 8 hours at 40°. The reaction mixture is then concentrated in vacuo; water is added to the residue and extraction is performed twice with methylene chloride. The organic phase is washed three times with water and twice with saturated sodium chloride solution; it is dried over sodium sulphate and concentrated in vacuo. The residue is triturated with ether, whereupon the reaction product is obtained in crystalline form. After filtration with suction and drying in vacuum, there is obtained 1-[2-(o-chlorobenzoyl)-4-chlorophenyl]-5-(morpholinomethyl)-1H-1,2,4-triazole-3-carboxylic acid methyl ester, m.p. 141°-143°.

The following are obtained in an analogous manner: with the use of 10.7 g (0.15 mole) of pyrrolidine there is yielded 1-[2-(o-chlorobenzoyl)-4-chlorophenyl]-5-[(1-pyrrolidinyl)-methyl]-1H-1,2,4-triazole-3-carboxylic acid methyl ester; with the use of 12.8 g (0.15 mole) of piperidine there is yielded 1-[2-(o-chlorobenzoyl)-4-chlorophenyl]-5-( piperidinomethyl)-1H-1,2,4-triazole-3-carboxylic acid methyl ester, and with the use of 11.0 g (0.15 mole) of diethylamine there is yielded 1-[2-(o-chlorobenzoyl)-4-chlorophenyl]-5-[(diethylamino)-methyl]-1H-1,2,4-triazole-3-carboxylic acid methyl ester.

The 1-[2-(o-chlorobenzoyl)-4-chlorophenyl]-5-(iodomethyl)-1H-1,2,4-triazole-3-carboxylic acid methyl ester required as starting material is produced as follows:
(a) 270 ml of a 6N solution of hydrogen chloride in methanol is added to a solution of 133.0 g (0.30 mole) of 1-[2-(o-chlorobenzoyl)-4-chlorophenyl]-5-(chloromethyl)-1H-1,2,4-trizole-3-carboxylic acid (crystals containing an equimolar amount of methanol; see German 'Offenlegungsschrift' No. 2,159,527, page 32) in 1400 ml of methanol, and the whole is refluxed for 18 hours. The reaction mixture is the concentrated in vacuo; water is added to the residue and extraction is performed twice with methylene chloride. The organic phase is washed once with saturated potassium bicarbonate solution, twice with water and once with saturated sodium chloride solution; it is subsequently dried over sodium sulphate and concentrated in vacuo. The residue is recrystallised from 1 liter of methanol. After drying there is obtained 1-[2-(o-chlorobenzoyl)-4-chlorophenyl]-5-(chloromethyl)-1H-1,2,4-triazole-3-carboxylic acid methyl ester, m.p. 130°-132°.
(b) A solution of 106.2 g (0.250 mole) of 1-[2-(o-chlorobenzoyl)-4-chlorophenyl]-5-chloromethyl)-1H-1,2,4-triazole-3-carboxylic acid methyl ester and 56.2 g (0.375 mole) of sodium iodide in 2200 ml of acetone is refluxed for 40 minutes. The reaction mixture is thereupon concentrated in vacuo. Water is added to the residue, and extraction is performed twice with methylene chloride. The organic phase is washed twice with diluted aqueous sodium bisulphite solution and twice with saturated sodium chloride solution; it is dried over sodium sulphate and concentrated in vacuo. The residue is dissolved in the minimum amount of methylene chloride, and 400 ml of ether is slowly added with stirring, whereupon the reaction product crystallises out. After filtration with suction and drying in vacuum, there is obtained 1-[2-(o-chlorobenzoyl)-4-chlorophenyl]-5-(iodomethyl)-1H-1,2,4-triazole-3-carboxylic acid methyl ester, m.p. 125°–128°.

EXAMPLE 14

A mixture of 12.90 g (0.025 mole) of 1-[2-(o-chlorobenzoyl)-4-chlorophenyl]-5-(iodomethyl)-1H-1,2,4-triazole-3-carboxylic acid methyl ester [see Example 13 (b)] and 11 ml of 33% ethanolic dimethylamine solution in 250 ml of methanol is stirred for 7 hours at room temperature. The reaction solution is thereupon concentrated in vacuo; water is added to the residue and the whole is extracted twice with methylene chloride. The organic phase is washed twice with water and once with saturated sodium chloride solution; it is dried over sodium sulphate and concentrated in vacuo to dryness. The amorphous residue is dissolved in 130 ml of ether; the solution is allowed to stand and the reaction product then crystallises out. It is filtered off with suction and washed with ether. After drying there is obtained 1-[2-(o-chlorobenzoyl)-4-chlorophenyl)-5-[(dimethylamino)-methyl]-1H-1,2,4-triazole-3-carboxylic acid methyl ester, m.p. 131°–134°.

EXAMPLE 15

28.5 g (0.06 mole) of 1-[2-(o-chlorobenzoyl)-4-chlorophenyl]-5-(morpholinomethyl)-1H-1,2,4-triazole-3-carboxylic acid methyl ester is covered over with 730 ml of methanol and 290 ml of concentrated aqueous ammonia solution. The mixture is heated, with stirring, for 4 hours at 40°, during which time the starting material slowly goes into solution. The reaction solution is then allowed to stand for 18 hours at room temperature and is subsequently concentrated in vacuo. Water is added to the residue and extraction is performed twice with ethyl acetate. The combined organic extracts are shaken with ice and sufficient 2N hydrochloric acid solution to bring the pH-value to 3. The hydrochloride, obtained in crystalline form, is washed with water and ethyl acetate. The acid aqueous layer is separated from the filtrate and combined with the suction-filter residue. There is then added 5N sodium hydroxide solution until the pH-value has reached 9, and the precipitated base is dissolved in methylene chloride. The methylene chloride solution is washed once with water and twice with saturated sodium chloride solution; it is dried over sodium sulphate and concentrated in vacuo. The residue is dissolved in a mixture of methylene chloride and isopropanol; the methylene chloride is evaporated off at normal pressure, and cooling to room temperature is effected. The crystalline reaction product is filtered off with suction and washed with isopropanol and ether. After drying in vacuum, the resulting 1-[2-(o-chlorobenzoyl)-4-chlorophenyl]-5-(morpholinomethyl)-1H-1,2,4-triazole-3-carboxamide melts at 165°–167°.

The following are obtained in an analogous manner:

from 27.6 g (0.06 mole) of 1-[2-(o-chlorobenzoyl)-4-chlorophenyl]-5-[(1-pyrrolidinyl)-methyl]-1H-1,2,4-triazole-3-carboxylic acid methyl ester there is obtained 1-[2-(o-chlorobenzoyl)-4-chlorophenyl]-5-[(1-pyrrolidinyl)-methyl]-1H-1,2,4-triazole-3-carboxamide;

from 28.4 g (0.06 mole) of 1-[2-o-chlorobenzoyl)-4-chlorophenyl]-5-(piperidinomethyl)-1H-1,2,4-triazole-3-carboxylic acid methyl ester there is obtained 1-[2-(o-chlorobenzoyl)-4-chlorophenyl]-5-(piperidinomethyl)-1H-1,2,4-triazole-3-carboxamide; and from 27.7 g (0.06 mole) of 1-[2-chlorobenzoyl)-4-chlorophenyl]-5-[(diethylamino)-methyl]-1H-1,2,4-triazole-3-carboxylic acid methyl ester there is obtained 1-[2-(o-chlorobenzoyl)-4-chlorophenyl]-5-[(diethylamino)-methyl]-1H-1,2,4-triazole-3-carboxamide, m.p. 150°–151°.

EXAMPLE 16

With the use of a solution of 20 g (about 0.65 mole) of methylamine in 120 ml of methanol, instead of the ammonia solution, there is obtained, with the procedure otherwise being analogous to that described in Example 15, N-methyl-1-[2-(o-chlorobenzoyl)-4-chlorophenyl]-5-(morpholinomethyl)-1H-1,2,4-triazole-3-carboxamide, m.p. 151°–153°.

There are obtained likewise analogously, starting with the given amounts of the further three methyl esters mentioned in Example 15:

N-methyl-1-[2-(o-chlorobenzoyl)-4-chlorophenyl]-5-[(1-pyrrolidinyl)-methyl]-1H-1,2,4-triazole-3-carboxamide;

N-methyl-1-[2-(o-chlorobenzoyl)-4-chlorophenyl]-5-(piperidinomethyl)-1H-1,2,4-triazole-3-carboxamide; and N-methyl-1-[2-(o-chlorobenzoyl)-4-chlorophenyl]-5-[(diethylamino)-methyl]-1H-1,2,4-triazole-3-carboxamide.

EXAMPLE 17

8.66 g (0.020 mole) of 1-[2-(o-chlorobenzoyl)-4-chlorophenyl)-5-[(dimethylamino)-methyl]-1H-1,2,4-triazole-3-carboxylic acid methyl ester is covered over with 400 ml of methanol and 80 ml of concentrated aqueous ammonia solution. The reaction solution is stirred for 16 hours at room temperature, and thereupon concentrated in vacuo to dryness. Water is added to the residue and extraction is performed twice with methylene chloride. The organic phase is washed twice with ice-cold 1N sodium hydroxide solution and is then extracted twice with 2N hydrochloric acid solution. To the aqueous acidified solutions there are added ice and sufficient 5N sodium hydroxide solution to bring the pH-value to 10. The precipitated base is taken up in methylene chloride. The organic phase is washed twice with water and once with saturated sodium chloride solution; it is dried over sodium sulphate and concentrated by evaporation to dryness. The amorphous residue is triturated with ether, whereupon the reaction product precipitates in crystalline form. It is filtered off with suction and washed with ether. After drying, there is obtained 1-[2-(o-chlorobenzoyl)-4-chlorophenyl]-5-[(dimethylamino)-methyl]-1H-1,2,4-triazole-3-carboxamide, m.p. 177°–180°.

There is obtained in an analogous manner, with the use of 6.5 g (0.21 mole) of methylamine in 40 ml of methanol instead of the concentrated aqueous ammonia solution, N-methyl-1-[2-(o-chlorobenzoyl)-4-chlorophenyl]-5-[(dimethylamino)-methyl]-1H-1,2,4-triazole-3-carboxamide, m.p. 153°–158°.

EXAMPLE 18

A mixture of 8.0 g (0.015 mole) of 1-[2-(o-chlorobenzoyl)-4-chlorophenyl]-5-(iodomethyl)-1H-1,2,4-triazole-3-carboxylic acid methyl ester [see Example 13 b)] and 3.3 ml of 1-methyl-piperazine in 160 ml of methanol is stirred for 16 hours at 40°. The reaction solution is then concentrated in vacuo; water is added to the residue and extraction is performed twice with methylene chloride. The organic phase is washed twice with icewater, and extraction is then performed twice with 2N hydrochloric acid solution. To the aqueous acidified extracts there are added ice and sufficient 5N sodium hydroxide solution to bring the pH-value to 10. The base that has precipitated is taken up in ether. The organic phase is washed twice with saturated sodium chloride solution; it is afterwards dried over sodium sulphate and concentrated in vacuo to dryness. There is obtained 1-[2-(o-chlorobenzoyl)-4-chlorophenyl]-5-[(4-methyl-1-piperazinyl)-methyl]-1H-1,2,4-triazole-3-carboxylic acid methyl ester as solidified foam.

The above crude product is covered over with 280 ml of methanol and 56 ml of concentrated aqueous ammonia solution. The reaction solution is stirred for about 15 hours at room temperature and is thereupon concentrated in vacuo. Water is added to the residue and extraction is performed twice with methylene chloride. The organic extracts are washed twice with ice-cold 1N sodium hydroxide solution, twice with water and once with saturated sodium chloride solution; they are dried over sodium sulphate and concentrated in vacuo to dryness. The residue is recrystallised from isopropanol. After drying, there is obtained 1-[2-o-chlorobenzoyl)-4-chlorophenyl]-5-[(4-methyl-1-piperazinyl)-methyl]-1H-1,2,4-triazole-3-carboxamide, m.p. 167°–169°.

EXAMPLE 19

2.50 ml (corresponding to 0.0067 mole of chromium trioxide) of an oxidation solution according to Jones (preparation of 250 ml by dissolving of 66.8 g of chromium trioxide in 57.5 ml of concentrated sulphuric acid and making up with water to 250 ml) is added dropwise at room temperature, with stirring, to a solution of 4.22 g (0.01 mole) of 1-[2-(α-hydroxybenzyl)-4-chlorophenyl]-5-[(dimethylamino)-methyl]-1H-1,2,4-triazole-3-carboxamide-hydrochloride in 800 ml of acetone. The reaction mixture, gradually assuming a green colour, is stirred for 18 hours at room temperature, and then concentrated in vacuo to 100 ml. Ice and saturated sodium carbonate solution are added until the pH-value has reached 10, and extraction is performed twice with ethyl acetate. The organic phase is washed twice with water and once with saturated sodium chloride solution and dried over magnesium sulphate. The drying agent is filtered off, and there is added to the filtrate ethereal hydrogen chloride solution until the pH-value has reached 3. The hydrochloride, precipitating in crystalline form, is filtered off with suction and washed with ethyl acetate and ether. After drying in vacuo, there is obtained 1-(2-benzoyl-4-chlorophenyl)-5-[(dimethylamino)-methyl]-1H-1,2,4-triazole-3-carboxamide-hydrochloride, m.p. 250° (with decomposition).

The starting material is produced as follows:

(a) 0.57 g (0.015 mole) of sodium borohydride is added all at once at 0°, with stirring, to the solution of 5.6 g (0.015 mole) of 1-(2-benzoyl-4-chlorophenyl)-5-(chloromethyl)-1H-1,2,4-triazole-3-carboxamide [see Example 1a)] in 250 ml of tetrahydrofuran and 25 ml of methanol, and the whole is subsequently stirred for a further hour at room temperature. There is then slowly added dropwise, with ice-water cooling, 1N hydrochloric acid solution until the pH-value of the reaction mixture has reached 4. The mixture obtained is concentrated in vacuo to dryness. Water is added to the residue, and extraction is performed twice with ethyl acetate. The organic phase is washed once with saturated potassium bicarbonate solution, twice with water and once with saturated sodium chloride solution; it is dried over sodium sulphate and concentrated in vacuo. There is obtained amorphous 1-[2-(α-hydroxybenzyl)-4-chlorophenyl]-5-(chloromethyl)-1H-1,2,4-triazole-3-carboxamide, which can be used directly in the next stage. On the silica gel plate, the compound has an Rf value of 0.61 in the system ethyl acetate/methanol (95:5).

(b) 6.8 ml of 33% ethanolic dimethylamine solution is added to a solution of 5.6 g (about 0.015 mole) of 1-[2-(α-hydroxybenzyl)-4-chlorophenyl]-5-(chloromethyl)-1H-1,2,4-triazole-3-carboxamide and 0.225 g of sodium iodide in 80 ml of methanol, and the whole is refluxed for 5 hours with stirring. The reaction mixture is thereupon concentrated in vacuo. Water and saturated sodium carbonate solution are added to the residue until the pH-value has reached 10, and extraction is performed twice with ethyl acetate. The organic phase is washed with water, and is then extracted three times with 1N hydrochloric acid solution. Sodium carbonate is added to the aqueous acidified extracts until the pH-value of 10 is obtained. The base that has precipitated is taken up in ether; the ether solution is washed twice with water and once with saturated sodium chloride solution; it is dried over sodium sulphate and concentrated in vacuo to yield amorphous 1-[2-(α-hydroxybenzyl)-4-chlorophenyl]-5-[(dimethylamino)-methyl]-1H-1,2,4-triazole-3-carboxamide. This is converted as follows into the crystalline hydrochloride: the crude base is dissolved in ethyl acetate, and ethereal hydrogen chloride solution is added until the pH-value is 4. The precipitated hydrochloride is filtered off with suction and washed with ethyl acetate and ether. After drying in vacuum, there is obtained 1-[2-(α-hydroxybenzyl) 4-chlorophenyl]-5-[(dimethylamino)-methyl]-1H-1,2,4-triazole-3-carboxamide-hydrochloride, m.p. 155°–157° (with decomposition).

EXAMPLE 20

The crude [1-[2-(α-hydroxybenzyl)-4-chlorophenyl]-5-[(dimethylamino)-methyl]-1H-1,2,4-triazol-3-yl]-methyl]-acetate (about 0.028 mole), obtained according to (b) [see below], is dissolved in 1500 ml of acetone, and there is then added dropwise to the solution at room temperature in the course of 30 minutes, with stirring, 7.20 ml (corresponding to 0.019 mole of chromium trioxide) of an oxidation solution according to Jones which is prepared by dissolving 66.8 g of chromium trioxide in 57.5 ml of concentrated sulphuric acid and making up with water to 250 ml. The colour of the reaction mixture changes from the initial yellow via reddish brown to a deep dark green. After completion of the dropwise addition, the reaction mixture is stirred for one hour at room temperature, and is thereupon concentrated in vacuo at 30° to the extent of 50%.

There are then added ice and saturated potassium bicarbonate solution until the pH-value reaches 8, and extraction is performed twice with ethyl acetate. The combined organic phases are extracted twice with 2 N hydrochloric acid solution. There are added to the aqueous acidified extracts ice and sufficient potassium carbonate to bring the pH-value to 8. The precipitated base is taken up in ethyl acetate. The organic phase is washed twice with water and once with saturated sodium chloride solution; it is dried over sodium sulphate and concentrated in vacuo to dryness. There is obtained crude [1-(2-benzoyl-4-chlorophenyl)-5-[(dimethylamino)-methyl]-1H-1,2,4-triazol-3-yl]-methyl]-acetate in the form of a slightly yellow oil.

A specimen of the crude product is dissolved in ether, and ethereal hydrogen chloride solution is added until the pH-value is 3. The hydrochloride, obtained in crystalline form, is filtered off with suction and, after drying, has a melting point of 166°–170°.

The starting material is produced as follows:

(a) 9.1 g (0.24 mole) of sodium borohydride is added portionwise at room temperature, with stirring, to a solution of 16.0 g (0.040 mole) of 1-(2-benzoyl-4-chlorophenyl)-5-[(dimethylamino)-methyl]-1H-1,2,4-triazole-3-carboxylic acid methyl ester [see Example 2] in 320 ml of tetrahydrofuran and 320 ml of methanol. The temperature of the reaction solution rises during the addition to 40°. The reaction mixture is subsequently heated for one hour at 50°; 100 ml of ice water is then added, and the bulk of the tetrahydrofuran and of the methanol is evaporated off in vacuo. The aqueous residue is extracted twice with ethyl acetate. The organic phase is washed once with 1 N sodium hydroxide solution, and is then extracted three times with 2 N hydrochloric acid solution. Sodium carbonate is added to the aqueous acidified extracts until the pH-value reaches 10. The precipitated base is dissolved in ethyl acetate; the solution is washed twice with water and once with saturated sodium chloride solution; it is dried over sodium sulphate and concentrated in vacuo. The residue is triturated with ether and hexane, whereupon the reaction product precipitates in crystalline form. After filtration with suction and drying in vacuum, there is obtained 1-[2-(α-hydroxybenzyl)-4-chlorophenyl]-5-[(dimethylamino)-methyl]-1H-1,2,4-triazole-3-methanol, m.p. 121°–123°.

(b) A solution of 3.0 ml (0.0318 mole) of acetic anhydride in 5 ml of methylene chloride is added dropwise at 0° within 10 minutes to the solution of 11.18 g (0.030 mole) of 1-[2-(α-hydroxybenzyl)-4-chlorophenyl]-5-[(dimethylamino)-methyl]-1H-1,2,4-triazole-3-methanol in 80 ml of methylene chloride and 10 ml of pyridine, and the whole is stirred for 20 hours at room temperature. There is then added a further 1.1 ml (0.012 mole) of acetic anhydride, and stirring is maintained for 4 hours at room temperature. The reaction mixture is concentrated in vacuo, and the residue is concentrated to dryness twice with toluene. The amorphous residue is dissolved in ethyl acetate, and the organic phase is washed twice with water and once with saturated sodium chloride solution. After drying over sodium sulphate and concentration in vacuo, there is obtained amorphous [1-[2-(α-hydroxybenzyl)-4-chlorophenyl]-5-[(dimethylamino)-methyl]-1H-1,2,4-triazol-3-yl]-methyl]-acetate, which can be used directly in the next step. To determine characteristic properties, a specimen of the crude product is dissolved in acetone, and a saturated solution of oxalic acid in acetone is added until the pH-value of 3 is reached. The oxalate, which has crystallised out, is filtered off with suction, and recrystallised from hot acetone. After drying, the oxalate melts at 185°–186° with decomposition.

EXAMPLE 21

60 ml of 1N sodium hydroxide solution (0.060 mole) is added at room temperature, with stirring, to a solution of 8.26 g (about 0.020 mole) of crude [[1-(2-benzoyl-4-chlorophenyl)-5-[(dimethylamino)-methyl]-1H-1,2,4-triazol-3-yl]-methyl]-acetate (see Example 20) in 250 ml of methanol and 115 ml of water. The temperature of the reaction solution rises to 33°. The reaction mixture is stirred for one hour at room temperature, and is subsequently concentrated in vacuo. Water is added to the residue, and extraction is performed twice with ethyl acetate. The combined organic phases are extracted three times with 2 N hydrochloric acid. There are added to the aqueous acidified extracts ice and sufficient sodium carbonate to bring the pH-value to 10. The precipitated base is taken up in ethyl acetate. The organic phase is washed twice with water and once with saturated sodium chloride solution; it is dried over sodium sulphate and concentrated in vacuo. There is obtained crude 1-(2-benzoyl-4-chlorophenyl)-5-[(dimethylamino)-methyl]-1H-1,2,4-triazole-3-methanol as solidified foam.

A specimen of the crude product is dissolved in ether, and ethereal hydrogen chloride solution is added until the pH-value is 3. The hydrochloride, obtained in crystalline form, is filtered off with suction and, after drying, melts at 198°–200° with decomposition.

EXAMPLE 22

2.63 ml (corresponding to 0.007 mole of chromium trioxide) of the oxidation solution according to Jones [see Example 20] is added dropwise at 0° to 5° with stirring, to a solution of 3.0 g (0.008 mole) of crude 1-(2-benzoyl-4-chlorophenyl)-5-[(dimethylamino)-methyl]-1H-1,2,4-triazole-3-methanol (see Example 21) in 670 ml of acetone. The reaction mixture, which assumes after some time a deep green colour, is stirred for 2 hours at room temperature, and afterwards concentrated in vacuo to the extent of 50%. There are then added ice and saturated sodium carbonate solution until the pH-value of 9 is obtained, and extraction is performed twice with ethyl acetate. The combined organic phases are washed twice with water and once with saturated sodium chloride solution; they are dried over sodium sulphate and concentrated in vacuo to dryness. The residue is dissolved in ethyl acetate/isopropanol (4:1), and the solution is chromatographed on a column of 200 g of silica gel. The eluant used is ethyl acetate/isopropanol (4:1). The fractions which contain the desired aldehyde are combined and concentrated by evaporation. There is obtained crude 1-(2-benzoyl-4-chlorophenyl)-5-[(dimethylamino)-methyl]-1H-1,2,4-triazole-3-carboxaldehyde as solidified foam.

A specimen of the aldehyde is dissolved in acetone, and a saturated solution of oxalic acid in acetone is added until the pH-value is 3. The oxalate precipitates in crystalline foam. It is filtered off with suction, washed well with acetone and ether and dried in vacuo; m.p. 178°–181° with foaming.

EXAMPLE 23

5.1 ml (corresponding to 0.0136 mole of chromium trioxide) of the oxidation solution according to Jones (see Example 20) is added dropwise at 0°, with stirring, to a solution of 3.79 g (0.001 mole) of 1-[2-(α-hydroxybenzyl)-4-chlorophenyl]-5-[(dimethylamino)-methyl]-3-methanol in 740 ml of acetone, and the whole, after completion of the dropwise addition, is stirred for a further 30 minutes at room temperature. The green reaction mixture is thereupon concentrated in vacuo to half its amount; ice water and saturated sodium carbonate solution are added until the pH-value reaches 9, and extraction is performed twice with ethyl acetate. The combined organic phases are washed twice with water and once with saturated sodium chloride solution; they are dried over sodium sulphate and concentrated in vacuo. The amorphous residue is dissolved in ethyl acetate/isopropanol (4:1), and the solution is chromatographed on a column of 250 g of silica gel. The eluant used is ethyl acetate/isopropanol (4:1). The fractions which contain the desired aldehyde are combined and concentrated by evaporation. The residue is dissolved in acetone, and a saturated solution of oxalic acid in acetone is added until the pH-value is 3. The oxalate, obtained in crystalline form, is filtered off with suction, and washed with acetone and ether. After drying, there is obtained 1-(2-benzoyl-4-chlorophenyl)-5-[(dimethylamino)-methyl]-1H-1,2,4-triazole-3-carboxaldehydeoxalate, m.p. 178°-181° with foaming.

EXAMPLE 24

A solution of 0.78 ml (0.01 mole) of methanesulphonic acid chloride in 8 ml of anhydrous methylene chloride is added dropwise at 0°, with stirring, to the solution of 2.0 g (0.005 mole) of crude 1-(2-benzoyl-4-chlorophenyl)-5-[(dimethylamino)-methyl]-1H-1,2,4-triazole-3-methanol in 66 ml of anhydrous methylene chloride and 1.33 ml of triethylamine, and the whole is stirred, without further cooling, for one hour. Ice water and 120 ml of methylene chloride are added to the reaction mixture; the aqueous phase is separated, and the organic phase is washed twice with ice-cold potassium bicarbonate solution and twice with saturated sodium chloride solution. After drying over magnesium sulphate and removal of the solvent by evaporation in vacuo, there remains the crude methane sulphonic acid ester of the starting material.

The crude methanesulphonic acid ester obtained above is dissolved in a mixture of 4.6 ml (0.03 mole) of 30% ethanolic dimethylamine solution and 60 ml of methanol, and the solution is allowed to stand for 16 hours. The reaction mixture is then evaporated in vacuo to dryness; there are added to the residue ice water and sufficient saturated sodium carbonate solution to bring the pH-value to 10; and extraction is performed three times with ethyl acetate. The organic phase is washed once with water, and is thereupon extracted three times with 2 N hydrochloric acid. Sodium carbonate is added to the acidified aqueous extracts until the pH-value is 10, and extraction is then performed twice with ethyl acetate. The combined ethyl acetate solutions are washed twice with water and once with saturated sodium chloride solution; they are dried over magnesium sulphate and filtered. There is added to the filtrate sufficient ethereal hydrogen chloride solution to bring the pH-value to 3. The product, precipitating in crystalline form, is filtered off with suction, and thoroughly washed with ethyl acetate and ether. After drying in vacuo, there is obtained 1-(2-benzoyl-4-chlorophenyl)-3,5-bis-[(dimethylamino)-methyl]-1H-1,2,4-triazole-dihydrochloride, m.p. 90° (with gradual decomposition).

EXAMPLE 25

A mixture of 4.18 g (0.01 mole) of 1-[2-(o-chlorobenzoyl)-4-chlorophenyl]-5-[(dimethylamine)-methyl]-1H-1,2,4-triazole-3-carboxamide and 2.86 g (0.015 mole) of p-toluenesulphonic acid chloride in 2.42 ml of pyridine and 24 ml of N,N-dimethylformamide is stirred for 2 hours at room temperature. The initially yellow colour of the reaction mixture changes during this time to green and then to red-brown. The reaction solution is poured into ice water, and extraction is performed twice with ether. The organic phase is washed three times with water and once with saturated sodium chloride solution; it is dried over sodium sulphate and concentrated in vacuo to dryness. The residue is crystallised from isopropanol. After filtration with suction followed by drying, there is obtained 1-[2-(0-chlorobenzoyl)-4-chlorophenyl]-5-[(dimethylamino)-methyl]-1H-1,2,4-triazole-3-carbonitrile, m.p. 117°-119°.

There is obtained analogously, from 3.84 g (0.01 mole) of 1-(2-benzoyl-4-chlorophenyl)-5-[(dimethylamino)-methyl]-1H-1,2,4-triazole-3-carboxamide, amorphous 1-(2-benzoyl-4-chlorophenyl)-5-[(dimethylamino)-methyl]-1H-1,2,4-triazole-3-carbonitrile. An addition is made to this compound in etheral solution of a solution of hydrogen chloride in ether, whereupon the crystalline hydrochloride precipitates; it is filtered with suction and washed with ether and hexane. After drying, the resulting 1-(2-benzoyl-4-chlorophenyl)-5-[(dimethylamino)-methyl]-1H-1,2,4-triazole-3-carbonitrile-hydrochloride melts at 216°-219° with decomposition.

EXAMPLE 26

150 ml of isopropanol is saturated at 0° with ammonia gas. To this solution there are added at 0°, with stirring, 2.45 g (0.05 mole) of sodium cyanide and, after 5 minutes, a solution of 3.69 g (0.01 mole) of crude 1-(2-benzoyl-4-chlorophenyl)-5-[(dimethylamino)-methyl]-1H-1,2,4-triazole-3-carboxaldehyde in 30 ml of isopropanol. There are then added at 0°, at intervals of 10 minutes, 2 portions each of 8.70 g (0.10 mole) of manganese dioxide, and the reaction mixture is stirred for 4 hours at 0°.

The reaction mixture is thereupon diluted with 250 ml of methylene chloride, and the whole is filtered through diatomaceous earth. The clear filtrate is concentrated in vacuo to dryness. The residue is dissolved in ethyl acetate/methanol (4:1), and the solution is chromatographed on a column of 300 g of silica gel. The eluant used is ethyl acetate/methanol (4:1). The fractions which contain the desired product are combined and concentrated by evaporation. The amorphous residue is dissolved in 50 ml of ethyl acetate, and ethereal hydrogen chloride solution is added until an acid reaction to Congo red is indicated. The hydrochloride, obtained in crystalline form, is filtered off with suction and washed with ethyl acetate and ether. After drying, the resulting 1-(2-benzoyl-4-chlorophenyl)-5-[(dimethylamino)-methyl]-1H-1,2,4-triazole-3-carboxamide-hydrochloride melts at 250° with decomposition.

The aldehyde required as starting material can be produced according to Example 22 or 23.

EXAMPLE 27

40 ml of 1 N sodium hydroxide solution is added to the solution of 5.37 g (0.01 mole) of crude [2-(dimethylamino)-acetamido-[2-(o-chlorobenzoyl)-4-chlorophenylazo]-malonic acid diethyl ester in 60 ml of methanol, and the reaction mixture is heated, with stirring, for 3 hours at 50°. The methanol is thereupon evaporated off in vacuo; the residue is diluted with 50 ml of water and 1 g of active charcoal is added. After filtration through purified diatomaceous earth, there is added to the clear filtrate 2 N hydrochloric acid solution until the pH-value is 7, and washing with methylene chloride is performed. The aqueous phase is then concentrated to dryness in vacuo, and the residue, to effect complete drying, is concentrated twice with methanol/toluene (1:1) in vacuo at 40°. The residue is subsequently boiled out with methanol. The undissolved inorganic salts are separated off by filtration through purified diatomaceous earth, and the clear filtrate is concentrated by evaporation to dryness. The residue consists of pure 1-[2-(o-chloro-benzoyl)-4-chlorophenyl]-5-[(dimethylamino)-methyl]-1H-1,2,4-triazole-3-carboxylic acid, which optionally can be used directly for the next step, the conversion into the methyl ester serving for its part, e.g., as starting material for Example 15.

For conversion into the hydrochloride, a saturated solution of hydrogen chloride in ether is added to a specimen of the carboxylic acid in ethanol until the pH-value of the mixture, after the addition of water, is 3. After the addition of ethyl acetate, the salt crystallises out. It is filtered off with suction and washed with ethyl acetate and hexane. After drying, the resulting 1-[2-(o-chlorobenzoyl)-4-chlorophenyl]-5-(dimethylamino-methyl)-1H-1,2,4-triazole-3-carboxylic acid-hydrochloride melts at 220° with decomposition.

For conversion into the methyl ester already mentioned, 10 ml of a 6 N solution of hydrogen chloride in methanol is added to a solution of 2.08 g (0.005 mole) of crude 1-[2-(o-chlorobenzoyl)-4-chlorophenyl]-5-(dimethylaminomethyl)-1H-1,2,4-triazole-3-carboxylic acid in 30 ml of methanol, and the whole is refluxed for 16 hours. The reaction mixture is thereupon concentrated in vacuo. Water is added to the residue, and extraction is performed twice with methylene chloride. The organic phase is washed twice with ice-cold 1N sodium bicarbonate solution and twice with saturated sodium chloride solution; it is dried over sodium sulphate and concentrated in vacuo. The residue crystallises out on trituration with ether. After filtration with suction and drying in vacuo, there is obtained pure 1-[2-(o-chlorobenzoyl)-4-chlorophenyl]-5-(dimethylaminomethyl)-1H-1,2,4-triazole-3-carboxylic acid methyl ester, m.p. 133°–135°.

The starting material for the first step (ring closure) is produced as follows:

(a) A solution of 5.02 g (0.02 mole) of (2-chloroacetamido)-malonic acid diethyl ester [see Ajay Kumar Bose, J.Indian Chem. Soc. 31, 108–110 (1954)] and 4.50 g (0.03 mole) of sodium iodide in 100 ml of acetone is refluxed for 30 minutes. The reaction mixture is thereupon concentrated in vacuo. Water is added to the residue, and extraction is performed twice with methylene chloride. The organic phase is washed once with diluted aqueous sodium bisulphite solution and twice with saturated sodium chloride solution; it is dried over sodium sulphate and concentrated in vacuo. The residue is recrystallised from methylene chloride/hexane. After filtration with suction and drying in vacuo, there is obtained (2-iodoacetamido)-malonic acid diethyl ester, m.p. 95°–97°.

(b) A mixture of 5.16 g (0.015 mole) of (2-iodoacetamido)-malonic acid diethyl ester and 8.0 ml (0.045 mole) of 33% ethanolic dimethylamine solution in 50 ml of ethanol is stirred for 16 hours at room temperature. The reaction solution is thereupon concentrated in vacuo; water is added to the residue and extraction is performed twice with ether. The organic phase is washed twice with ice water and once with saturated sodium chloride solution; it is dried over sodium sulphate and concentrated in vacuo. The residue, a viscous oil, is practically pure [2-(dimethylamino)-acetamido]-malonic acid diethyl ester, and is used directly for the next step.

(c) A solution of 4.53 g (0.017 mole) of 2-amino-2',5-dichloro-benzophenone [see L. H. Sternbach et al., J. Org. Chem. 26, 4448 (1961)] in 21 ml of glacial acetic acid/conc. hydrochloric acid (4:1) is diazotised at room temperature, with stirring, with 3.4 ml (0.014 mole) of 5-molar aqueous sodium nitrite solution. The diazonium salt solution obtained is cooled to 10°; 9 g of ice is added thereto and there is then quickly added dropwise a solution of 4.43 g (0.017 mole) of crude [2-(dimethyl-amino)-acetamido]-malonic acid diethyl ester in 44 ml of acetone. There is subsequently added dropwise at 5°–10°, within 15 minutes, a saturated aqueous potassium carbonate solution until the pH-value is 6. Stirring is maintained for a further hour at room temperature, and 150 ml of ether is then added. The ether layer is separated, and washed twice with ice water and once with saturated sodium chloride solution; it is dried over sodium sulphate and concentrated in vacuo. The residue, a yellow-brown oil, consists of practically pure [2-(dimethylamino)-acetamido]-[2-(o-chlorobenzoyl)-4-chlorophenylazo]-malonic acid diethyl ester. The compound shows on silica gel thin-layer plates an Rf-value of 0.36 in the system toluene/ethyl acetate (1:1).

EXAMPLE 28

A solution of 5.37 g (0.01 mole) of crude [2-(dimethylamino)-acetamido]-[2-(o-chlorobenzoyl)-4-chlorophenylazo]-malonic acid diethyl ester [see Example 27 (a) to (c)] and 50 ml of conc. aqueous ammonia solution in 100 ml of methanol is stirred for 16 hours at room temperature. The reaction mixture is thereupon concentrated in vacuo. Water is added to the residue and extraction is performed twice with methylene chloride. The organic phase is extracted twice with ice-cold 1 N hydrochloric acid. To the acid aqueous extraction there is added 5 N sodium hydroxide solution until the pH-value has reached 11; and the formed dispersion of the reaction product is extracted twice with methylene chloride. The organic phase is washed twice with water and once with saturated sodium chloride solution; it is dried over sodium sulphate and concentrated in vacuo to dryness. The residue crystallises out on trituration with ether. After filtration with suction and drying in vacuo, there is obtained, as a result of decarbethoxylation, ring closure and ammonolysis of the ester group remaining, performed in the same operation, 1-[2-(o-chlorobenzoyl)-4-chlorophenyl]-5-[(dimethylamino)- methyl)-1H-1,2,4-triazole-3-carboxamide, m.p. 178°-180°.

EXAMPLE 29

4.0 ml of a 33% ethanolic dimethylamine solution is added to a mixture of 4.37 g (0.01 mole) of crude N-ethyl-1-[2-(o-chlorobenzoyl)-4-chlorophenyl]-1H-1,2,4-triazole-3-carboxamide and 0.15 g of sodium iodide in 80 ml of methanol, and the mixture is refluxed, with stirring, for 4 hours. The reaction mixture is thereupon concentrated in vacuo. Water and saturated sodium carbonate solution are added to the residue until the pH value has reached 10 and extraction is performed twice with ethyl acetate. The organic phase is washed with water and saturated sodium chloride solution, dried over sodium sulphate and then concentrated in vacuo. The residue is recrystallised from isopropanol to obtain, after drying in vacuo, N-ethyl-1-[2-(o-chlorobenzoyl)-4-chlorophenyl]-5-[(dimethylamino)-methyl]-1H-1,2,4-triazole-3-carboxamide, m.p. 131°-133°.

In an analogous manner is obtained, from 4.51 g of crude N-propyl-1-[2-(o-chlorobenzoyl)-4-chlorophenyl]-5-(chloromethyl)-1H-1,2,4-triazole-3-carboxamide: N-propyl-1-[2-(o-chlorobenzoyl)-4-chlorophenyl]-5-[(dimethylamino)-methyl]-1H-1,2,4-triazole-3-carboxamide, m.p. 110°-113° (from ether).

The starting material is produced as follows: 8.95 g (0.02 mole) of 1-[2-(o-chlorobenzoyl)-4-chlorophenyl]-5-(chloromethyl)-1H-1,2,4-triazole-3-carboxylic acid (contains one molecule of crystal methanol; see DOS 2,159,527, p. 32) is covered over with 40 ml of oxalyl chloride and refluxed for one hour. The clear yellow solution is concentrated at 40° in vacuo, and, to effect the complete removal of the oxalyl chloride, 100 ml of toluene is added and the solution is again concentrated at 40° in vacuo.

The resulting crude 1-[2-(o-chlorobenzoyl)-4-chlorophenyl]-5-(chloromethyl)-1H-1,2,4-triazole-3-carbonyl chloride is dissolved in 80 ml of dioxane, and to the solution is added dropwise at room temperature, in the course of 30 minutes, a solution of 1.98 g (0.044 mole) of ethylamine in 30 ml of dioxane. The ethylamine hydrochloride gradually precipitates out. The reaction mixture is concentrated in vacuo to dryness. Ice water and ether are added to the residue; the organic phase is separated and is washed successively with cold 1 N hydrochloric acid, with cold 0.1 N sodium hydroxide solution and with saturated sodium chloride solution. After drying, and concentration in vacuo, is obtained crude N-ethyl-1-[2-(o-chlorobenzoyl)-4-chlorophenyl]-5-(chloromethyl)-1H-1,2,4-triazole-3-carboxamide.

In an analogous manner there is obtained, from 8.95 g of 1-[2-(o-chlorobenzoyl)-4-chlorophenyl]-5-(chloromethyl)-1H-1,2,4-triazole-3-carboxylic acid (contains one molecule of crystal methanol), by way of the acid chloride with the use of 2.60 g of n-propylamine: crude N-propyl-1-[2-(o-chlorobenzoyl)-4-chlorophenyl]-5(chloromethyl)-1H-1,2,4-triazole-3- carboxamide.

EXAMPLE 30

23 ml of 36% aqueous formaldehyde solution is added to the solution of 11.5 g (0.03 mole) of N-ethyl-6-(o-chlorophenyl)-8-chloro-4H-s-triazolo[1,5-a][1,4]benzodiazepine-2-carboxamide in 39 ml of 85% commercial formic acid, and the mixture is heated, with stirring, for 4 hours at 100°. The reaction solution is thereupon poured into ice water, and undesired neutral constituents are extracted with ether. To the acid aqueous phase is added concentrated sodium hydroxide solution until the pH value has reached 11. The precipitated crude product is taken up in ether. The organic extracts are washed twice with water and once with saturated sodium chloride solution; they are dried over sodium sulphate and concentrated in vacuo. The residue is recrystallised from isopropanol to obtain, after drying in vacuo, N-ethyl-1-[2-(o-chlorobenzoyl)-4-chlorophenyl]-5-[(dimethylamino)-methyl]-1H-1,2,4-triazole-3-carboxamide, m.p. 131°-133° C.

In an analogous manner there is obtained, from 11.9 g of N-propyl-6-(o-chlorophenyl)-8-chloro-4H-s-triazolo[1,5-a][1,4]benzodiazepine-2-carboxamide: N-propyl-1-[2-(o-chlorobenzoyl)-4-chlorophenyl]-5-[(dimethylamino)-methyl]-1H-1,2,4-triazole-3-carboxamide, m.p. 110°-113° (from ether).

EXAMPLE 31

35.0 g (0.0835 mole) of 1-[2-(o-chlorobenzoyl)-4-chlorophenyl]-5-[(dimethylamino)-methyl]-1H-1,2,4-triazole-3-carboxylic acid is refluxed in 175 ml of thionyl chloride for 90 minutes. The clear solution is concentrated at 40° in vacuo and the residue, for complete removal of the thionyl chloride, is dissolved in 100 ml of absolute toluene and the solution is again concentrated by evaporation. The resulting crude acid chloride hydrochloride is dissolved in 350 ml of dioxane; an addition is made at room temperature, with stirring, of 56.7 ml (0.417 mole) of 33% ethanolic ethylamine solution, and stirring is continued at room temperature for 18 hours. The reaction mixture is thereupon concentrated in vacuo to dryness. To the residue is added ice water, and 2 N sodium hydroxide solution is added until the pH value has reached 11. The precipitated crude product is taken up in methylene chloride. The separated organic extracts are washed twice with water and once with saturated sodium chloride solution; they are then dried over sodium sulphate and concentrated in vacuo. The solid residue is recrystallised from 500 ml of isopropanol. After drying in vacuo, the resulting N-ethyl-1-[2-(o-chlorobenzoyl)-4-chlorophenyl]-5-[(dimethylamino)-methyl]-1H-1,2,4-triazole-3-carboxamide melts at 131°-133°.

The starting material is produced as follows:
310 ml (0.226 mole) of a 33% ethanolic dimethylamine solution is added to a suspension of 45.0 g (0.11 mole) of 1-[2-(o-chlorobenzoyl)-4-chlorophenyl]-5-(chloromethyl)-1H-1,2,4-triazole-3-carboxylic acid (see DT-OS 2,159,527, page 32) and 0.5 g (0.0033 mole) of sodium iodide in 250 ml of methanol, and the mixture is stirred for 6 hours at room temperature. The clear reaction solution is concentrated in vacuo; the residue is dissolved in 200 ml of water, and 2 N hydrochloric acid solution is slowly added until the pH value of 5 is reached. After 16 hours' standing at 0°-5°, the precipitated aminic acid is filtered off and well washed with water and then with ether. Upon drying, there is obtained 1-[2-(o-chlorobenzoyl)-4-chlorophenyl]-5-[(dimethylamino)-methyl]-1H-1,2,4-triazole-3-carboxylic acid, m.p. 222°-225° with decomposition.

In an analogous manner there is obtained: N-propyl-1-[2-(o-chlorobenzoyl)-4-chlorophenyl]-5-[(dimethylamino)-methyl]-1H-1,2,4-triazole-3-carboxamide, m.p. 110°-113° (from ether).

What we claim is:
1. A triazole derivative of the formula I

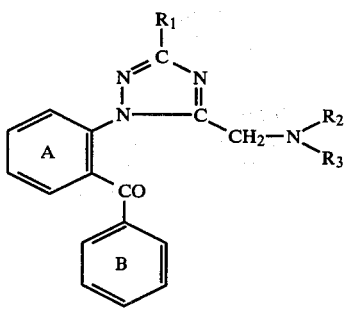

wherein
$R_1$ represents a group of the partial formula I aa

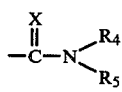

in which X represents oxygen and $R_4$ and $R_5$ each independently represent hydrogen, lower alkyl having at most 3 carbon atoms, or together with the adjacent nitrogen atom, they represent morpholino, 1-pyrrolidinyl, or piperidino, $R_2$ represents lower alkyl, $R_3$ represents hydrogen or lower alkyl or together with the adjacent nitrogen atom they represent morpholino, 1-pyrrolidinyl or piperidino the rings A and B independently of each other are unsubstituted or substituted by halogen up to atomic number 35, trifluoromethyl, nitro, lower alkyl or lower alkoxy and its pharmaceutically acceptable acid addition salts.

2. A compound according to claim 1 having the formula I given in claim 1 in which
$R_1$ represents a group of the partial formula I aa, and the rings A and B are independently of each other unsubstituted, or substituted by halogen up to atomic number 35, trifluoromethyl or nitro, and its pharmaceutically acceptable acid addition salts.

3. A compound according to claim 1 having the formula I given in claim 1, in which $R_1$ represents a group of the partial formula I aa in which X represents an oxygen atom, and $R_4$ and $R_5$ each independently represent hydrogen, lower alkyl having at most 3 carbon atoms, or together with the adjacent nitrogen atom they represent morpholino, 1-pyrrolidinyl or piperidino, $R_2$ and $R_3$ represent lower alkyl having at most 2 carbon atoms, or together with the adjacent nitrogen atom they represent morpholino, 1-pyrrolidinyl or piperidino, ring A is substituted in the 4-position with respect to the triazole ring by halogen up to atomic number 35 or by nitro, and ring B is unsubstituted or substituted by halogen up to atomic number 35 in the ortho-position, and its pharmaceutically acceptable acid addition salts.

4. A compound according to claim 1, which is 1-[2-(o-chlorobenzoyl)-4-chlorophenyl]-5-(morpholinomethyl)-1H-1,2,4-triazole-3-carboxamide and its pharmaceutically acceptable acid addition salts.

5. A compound according to claim 1, which is 1-[2-(o-chlorobenzoyl)-4-chlorophenyl]-5-[(dimethylamino)-methyl]-1H-1,2,4-triazole-3-carboxamide and its pharmaceutically acceptable acid addition salts.

6. A compound according to claim 1, which is N-methyl-1-[2-(o-chlorobenzoyl)-4-chlorophenyl]-5-[(dimethylamino)-methyl]-1H-1,2,4-triazole-3-carboxamide, and its pharmaceutically acceptable acid addition salts.

7. A compound according to claim 1, which is N-ethyl-1-[2-(o-chlorobenzoyl)-4-chlorophenyl]-5-[(dimethylamino)-methyl]-1H-1,2,4-triazole-3-carboxamide, and its pharmaceutically acceptable acid addition salts.

8. A compound according to claim 1, which is N-propyl-1-[2-(o-chlorobenzoyl)-4-chlorophenyl]-5-[(dimethylamino)-methyl]-1H-1,2,4-triazole-3-carboxamide, and its pharmaceutically acceptable acid addition salts.

9. A compound according to claim 1, which is N-methyl-1-[2-(o-chlorobenzoyl)-4-chlorophenyl]-5-(morpholino-methyl)-1H-1,2,4-triazole-3-carboxamide, and its pharmaceutically acceptable acid addition salts.

10. A compound according to claim 1, which is N-ethyl-1-[2-(o-chlorobenzoyl)-4-chlorophenyl]-5-(morpholino-methyl)-1H-1,2,4-triazole-3-carboxamide, and its pharmaceutically acceptable acid addition salts.

11. A compound according to claim 1, which is N,N-dimethyl-1-[2-(o-chlorobenzoyl)-4-chlorophenyl]-5-[(dimethylamino)-methyl]-1H-1,2,4-triazole-3-carboxamide and its pharmaceutically acceptable acid addition salts.

12. A compound according to claim 1, which is N,N-dimethyl-1-[2-(o-fluorobenzoyl)-4-chlorophenyl]-5-[(dimethylamino)-methyl]-1H-1,2,4-triazole-3-carboxamide and its pharmaceutically acceptable acid addition salts.

13. A pharmaceutical composition useful in the treatment of epilepsy and of conditions of tension and of agitation in a warm-blooded animal comprising a therapeutically effective amount of a compound according to claim 1 which corresponds to the formula I

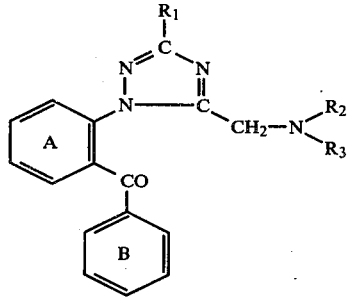

wherein
$R_1$ represents a group of the partial formula I as

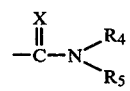

in which X represents oxygen and $R_4$ and $R_5$ each independently represent hydrogen, lower alkyl having at most 3 carbon atoms, or together with the adjacent nitrogen atom, they represent morpholino, 1-pyrrolidinyl, or piperidino, $R_2$ represents lower alkyl, $R_3$ represents hydrogen or lower alkyl or together with the adjacent nitrogen atom they represent morpholino, 1-pyrrolidinyl or piperidino the rings A and B independently of each other are unsubstituted or substituted by halogen up to atomic number 35, trifluoromethyl, nitro, lower alkyl or lower alkoxy and its pharmaceutically acceptable acid addition salts, together with a pharmaceutical carrier.

14. The pharmaceutical composition of claim 13 wherein a compound of formula I given in claim 13, in which R₁ represents a group of the partial formula I aa

wherein X represents oxygen, and R₂, R₃, R₄ and R₅ have the meanings given in claim 13 and the rings A and B are independently of each other unsubstituted, or substituted by halogen up to atomic number 35, trifluoromethyl or nitro, and its pharmaceutically acceptable acid addition salts.

15. A pharmaceutical composition according to claim 13, wherein a compound of formula I given in claim 13, in which R₁ represents a group of the partial formula I aa, in which X represents oxygen, and R₄ and R₅ each independently represent hydrogen, lower alkyl having at most 3 carbon atoms, or together with the adjacent nitrogen atom they represent morpholino, 1-pyrrolidinyl, or piperidino, R₂ and R₃ represent lower alkyl having at most 2 carbon atoms, or together with the adjacent nitrogen atom they represent morpholino, 1-pyrrolidinyl, or piperidino, ring A is substituted in the 4-position with respect to the triazole ring by halogen up to atomic number 35 or by nitro, and ring B is unsubstituted or substituted by halogen up to atomic number 35 in the ortho-position, or a pharmaceutically acceptable acid addition salt thereof is present.

16. A pharmaceutical composition according to claim 13, wherein 1-[2(o-chlorobenzoyl)-4-chlorophenyl]-5-(morpholinomethyl)-1H-1,2,4-triazole-3-carboxamide, or a pharmaceutically acceptable acid addition salt thereof is present.

17. A pharmaceutical composition according to claim 13, wherein N-ethyl-1-[2-(o-chlorobenzoyl)-4-chlorophenyl]-5-[(dimethylamino)-methyl]-1H-1,2,4-triazole-3-carboxamide, or a pharmaceutically acceptable acid addition salt thereof is present.

18. A method of the treatment of epilepsy and of conditions of tension and of agitation in a warm-blooded animal comprising administration to said animal of a therapeutically effective amount of a compound according to claim 1 which corresponds to the formula I given in claim 1, or of a pharmacologically acceptable acid addition salt thereof.

19. A method according to claim 18 comprising administration of a therapeutically effective amount of 1-[2-(o-chlorobenzoyl)-4-chlorophenyl]-5-(morpholinomethyl-1H-1,2,4-triazole-3-carboxamide, or of a pharmacologically acceptable acid addition salt thereof.

20. A method according to claim 18 comprising administration of a therapeutically effective amount of N-ethyl-1-[2-(o-chlorobenzoyl)-4-chlorophenyl)-5-[(dimethylamino)-methyl]-1H-1,2,4-triazole-3-carboxamide, or a pharmaceutically acceptable acid addition salt thereof is present or of a pharmacologically acceptable acid addition salt thereof.

* * * * *